(12) United States Patent
Herold et al.

(10) Patent No.: US 7,786,307 B2
(45) Date of Patent: Aug. 31, 2010

(54) AMINO ALCOHOL DERIVATIVES AND THEIR ACTIVITY AS RENIN INHIBITORS

(75) Inventors: Peter Herold, Basel (CH); Stefan Stutz, Basel (CH); Aleksandar Stojanovic, Basel (CH); Vincenzo Tschinke, Binningen (CH); Christiane Marti, Baden (CH); Michael Quirmbach, Basel (CH)

(73) Assignee: Novartis AG, Basel (CH)

( * ) Notice: Subject to any disclaimer, the term of this patent is extended or adjusted under 35 U.S.C. 154(b) by 430 days.

(21) Appl. No.: 10/587,150

(22) PCT Filed: Jan. 21, 2005

(86) PCT No.: PCT/EP2005/050274

§ 371 (c)(1),
(2), (4) Date: Jul. 24, 2006

(87) PCT Pub. No.: WO2005/070871

PCT Pub. Date: Aug. 4, 2005

(65) Prior Publication Data

US 2007/0155743 A1    Jul. 5, 2007

(30) Foreign Application Priority Data

Jan. 23, 2004    (CH) .................................... 0096/04

(51) Int. Cl.
*C07D 211/26*    (2006.01)
*A61K 31/445*    (2006.01)

(52) U.S. Cl. ...................................... 546/229; 514/331
(58) Field of Classification Search ................. 546/229; 514/331

See application file for complete search history.

(56) References Cited

U.S. PATENT DOCUMENTS 6,436,980 B1 * 8/2002 Leger et al. ................. 514/375

2007/0021399 A1 * 1/2007 Herold et al. ............... 514/183
2007/0021400 A1 * 1/2007 Herold et al. ............... 514/183

FOREIGN PATENT DOCUMENTS

EP    0 519 433    12/1992
WO    02/40007    5/2002

OTHER PUBLICATIONS

Nussberger et al J. Cardiovascular Pharmacol. 1987, vol. 9—abstract.*
P. Raddatz et al., "Renin Inhibitors Containing New P1-P1' Dipeptide Mimetics with Heterocycles in P1'", Journal of Medicinal Chemistry, American Chemical Society, vol. 35, No. 19, pp. 3525-3536, XP002050635, ISSN: 0022-2623, Sep. 18, 1992.
K. Allikmets, "Aliskiren Speedel", Current Opinion in Investigational Drugs, Pharmapress, U.S., vol. 3, No. 10, pp. 1479-1482, XP009017210, ISSN: 1472-4472, 2002.
J.M. Wood et al., "Structure-based design of aliskiren, a novel orally effective renin inhibitor", Biochemical and Biophysical Research Communications, Academic Press Inc., vol. 308, No. 4, pp. 698-705, XP004447169, ISSN: 0006-291X, Sep. 5, 2003.

* cited by examiner

*Primary Examiner*—Rita J Desai
*Assistant Examiner*—John Mabry
(74) *Attorney, Agent, or Firm*—Wenderoth, Lind & Ponack, L.L.P.

(57) ABSTRACT

The application relates to novel amino alcohols of general formula (I) where R, $R_1$, $R_2$, $R_3$, $R_4$, $R_5$, $X_1$ and $X_2$ each have the definitions illustrated in detail in the description, to a process for their preparation and to the use of these compounds as medicines, in particular as renin inhibitors.

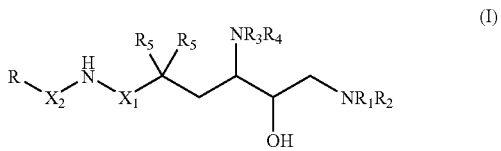

(I)

2 Claims, No Drawings

AMINO ALCOHOL DERIVATIVES AND THEIR ACTIVITY AS RENIN INHIBITORS

The invention relates to novel amino alcohols, to processes for preparing the inventive compounds, to pharmaceutical preparations comprising them and to their use as active ingredients of medicaments, in particular as renin inhibitors.

Amino-compounds showing renin-inhibiting properties are known, for example from EP519433.

Firstly, the present invention provides compounds of the general formula

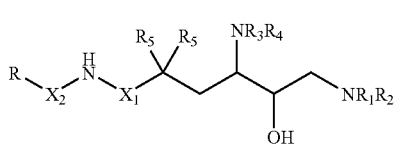

(I)

where $R_1$ is a) hydrogen, hydroxyl or amino; or
is b) $C_1$-$C_8$-alkyl, $C_3$-$C_8$-cycloalkyl, $C_1$-$C_8$-alkanoyl, $C_1$-$C_8$-alkoxycarbonyl, aryl-$C_0$-$C_4$-alkyl or heterocyclyl-$C_0$-$C_4$-alkyl, which radicals may be substituted by 1-4 $C_1$-$C_8$-alkyl, halogen, cyano, oxide, oxo, trifluoromethyl, $C_1$-$C_8$-alkoxy, $C_1$-$C_8$-alkoxycarbonyl, aryl or heterocyclyl;

$R_2$ is a) $C_1$-$C_8$-alkyl, $C_3$-$C_8$-cycloalkyl, $C_1$-$C_8$-alkylsulphonyl, $C_3$-$C_8$-cycloalkylsulphonly, aryl-$C_0$-$C_8$-alkylsulphonyl, heterocyclylsulphonyl, $C_3$-$C_{12}$-cycloalkyl-$C_1$-$C_8$-alkanoyl, $C_3$-$C_{12}$-cycloalkyl-$C_3$-$C_8$-cycloalkanoyl, aryl-$C_1$-$C_8$-alkanoyl, aryl-$C_3$-$C_8$-cycloalkanoyl, $C_1$-$C_8$-alkanoyl, $C_1$-$C_8$-alkoxycarbonyl, optionally N-mono- or N,N-di-$C_1$-$C_8$-alkylated carbamoyl-$C_0$-$C_8$-alkyl, aryl-$C_0$-$C_4$-alkyl or heterocyclyl-$C_0$-$C_4$-alkyl, which radicals may be substituted by 1-4 $C_1$-$C_8$-alkyl, $C_3$-$C_8$-cycloalkyl, $C_3$-$C_8$-cycloalkoxy, amino, $C_{1-5}$-alkylamino, di-$C_{1-6}$-alkylamino, $C_0$-$C_6$-alkylcarbonylamino, halogen, cyano, hydroxyl, oxide, oxo, trifluoromethyl, $C_1$-$C_8$-alkoxy, optionally N-mono- or N,N-di-$C_1$-$C_8$-alkylated carbamoyl, $C_1$-$C_8$-alkoxycarbonyl, $C_{1-6}$-alkylene-dioxy, aryl or heterocyclyl; or
is b) together with $R_1$ and the nitrogen atom to which they are bonded, a saturated or partly unsaturated 4-8-membered heterocyclic ring which may contain an additional nitrogen, oxygen or sulphur atom or an —SO— or —SO2- group, in which case the additional nitrogen atom may optionally be substituted by $C_1$-$C_8$-alkyl, $C_1$-$C_8$-alkanoyl, $C_1$-$C_8$-alkoxycarbonyl, aryl or heterocyclyl radicals, and this heterocyclic ring may be part of a bicyclic or tricyclic ring system having a total of up to 16 members, and the second ring may also contain a nitrogen, oxygen or sulphur atom or an —SO— or —SO2- group, and the nitrogen atom of the second ring may optionally be substituted by $C_1$-$C_8$-alkyl, $C_1$-$C_8$-alkanoyl, $C_1$-$C_8$-alkoxycarbonyl, aryl or heterocyclyl radicals and all ring systems mentioned may be substituted by 1-4 $C_1$-$C_8$-alkyl, halogen, hydroxyl, oxide, oxo, cyano, trifluoromethyl, $C_1$-$C_8$-alkoxy, $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonylamino, $C_1$-$C_8$-alkylcarbonylamino, $C_1$-$C_8$-alkylamino, N,N-di-$C_1$-$C_8$-alkylamino, aryl-$C_0$-$C_4$-alkyl, aryloxy-$C_0$-$C_4$-alkyl, aryl-$C_0$-$C_4$-alkyl-$C_1$-$C_8$-alkoxy, aryloxy-$C_0$-$C_4$-alkyl-$C_1$-$C_8$-alkoxy, heterocyclyl-$C_0$-$C_4$-alkyl, heterocyclyloxy-$C_0$-$C_4$-alkyl, heterocyclyl-$C_0$-$C_4$-alkyl-$C_1$-$C_8$-alkoxy or heterocylyloxy-$C_0$-$C_4$-alkyl-$C_1$-$C_8$-alkoxy;

$R_3$ is hydrogen, $C_1$-$C_8$-alkyl, $C_1$-$C_8$-alkoxycarbonyl or $C_1$-$C_8$-alkanoyl;

$R_4$ is hydrogen, $C_1$-$C_8$-alkyl, $C_1$-$C_8$-alkoxycarbonyl or $C_1$-$C_8$-alkanoyl;

$R_5$ are each independently hydrogen or $C_1$-$C_8$-alkyl, or, together with the carbon atom to which they are bonded, are a $C_3$-$C_8$-cycloalkylidene radical;

R is an optionally substituted unsaturated carbocyclic or heterocyclic radical;

one of the $X_1$ and $X_2$ radicals is carbonyl and the other is methylene;

and salts thereof.

Possible substituents for R are aliphatic, araliphatic, heterocycloaliphatic-aliphatic or heteroaliphatic radicals, optionally esterified or amidated carboxyl, optionally aliphatically or heteroaliphatically substituted amino or else optionally aliphatically, araliphatically, heterocycloaliphatic-aliphatically or heteroarylaliphatically etherified hydroxyl.

In the context of the above definitions, the above general terms preferably have the following definitions:

Aliphatic radicals are, for example, lower alkyl, hydroxy (lower alkyl), (lower alkanoyl)oxy (lower alkyl), (lower alkoxy)(lower alkyl), (lower alkoxy)(lower alkoxy)(lower alkyl), an optionally amidated carboxyl or carboxy(lower alkyl) group, optionally esterified or amidated dicarboxy (lower alkyl), optionally esterified or amidated carboxy(hydroxy)(lower alkyl), (lower alkane)sulphonyl(lower alkyl) or optionally N-mono- or N,N-di(lower alkyl)ated sulphamoyl (lower alkyl).

Optionally aliphatically, araliphatically, heterocycloaliphatic-aliphatically or heteroaryl-aliphatically etherified hydroxyl is, for example, hydroxyl, lower alkoxy, hydroxy(lower alkoxy), (lower alkanoyl)oxy(lower alkoxy), (lower alkoxy)(lower alkoxy), (lower alkoxy)(lower alkoxy)-(lower alkoxy), polyhalo(lower alkoxy), cyano(lower alkoxy), an amino(lower alkoxy) radical which is optionally N-(lower alkanoyl)ated, N-mono- or N,N-di(lower alkyl) ated, or is N,N-disubstituted by lower alkylene, hydroxy-, (lower alkoxy)- or (lower alkoxy)(lower alkoxy)-(lower alkylene), or by optionally N'-(lower alkanoyl)ated aza(lower alkylene), oxa(lower alkylene) or optionally S-oxidized thia (lower alkylene), each of which is optionally N-(lower alkanoyl)ated or is N'-substituted or N'-(lower alkyl)ated by (lower alkoxy)carbonyl or (lower alkoxy)(lower alkyl), optionally substituted phenyl- or pyridyl(lower alkoxy), optionally amidated caboxyl or carboxy(lower alkoxy) or tetrazolyl(lower alkoxy).

Heteroaliphatic radicals are, for example, optionally N-(lower alkanoyl)ated, N-mono- or N,N-di(lower alkyl) ated, or amino(lower alkyl) radicals N,N-disubstituted by lower alkylene, hydroxy-, (lower alkoxy)- or (lower alkoxy) (lower alkoxy)(lower alkylene), or by aza(lower alkylene), oxa(lower alkylene) or optionally S-oxidized thia(lower alkylene), each of which is optionally N'-(lower alkanoyl)ated or is N'-substituted or N'-(lower alkyl)ated by (lower alkoxy)carbonyl or (lower alkoxy)(lower alkyl), or N-mono- or N,N-di(lower alkyl)ated thiocarbamoyl(lower alkyl) radicals.

Araliphatic or heteroarylaliphatic radicals are, for example, optionally substituted phenyl- or pyridinyl(lower alkyl) groups.

Cycloaliphatic-aliphatic radicals are, for example, cycloalkyl(lower alkyl) or optionally esterified or amidated carboxycycloalkyl(lower alkyl).

Optionally aliphatically substituted amino is, for example, optionally N-(lower alkanoyl)ated or N-mono- or N,N-di(lower alkyl)ated amino.

Optionally heteroaliphatically substituted amino is, for example, amino which is optionally N-(lower alkanoyl)ated, N-mono- or N,N-di(lower alkyl)ated, or N,N-disubstituted by lower alkylene, hydroxy-, (lower alkoxy)-, (lower alkoxy)carbonyl- or (lower alkoxy)(lower alkoxy)-(lower alkylene), or by optionally N'-(lower alkanoyl)ated aza(lower alkylene), oxa(lower alkylene) or optionally S-oxidized thia(lower alkylene), each of which is optionally N'-substituted or N'-(lower alkyl)ated by (lower alkoxy)carbonyl or (lower alkoxy)(lower alkyl).

Optionally esterified or amidated carboxyl is, for example, optionally aliphatically or araliphatically etherified carboxyl or aliphatically substituted carbamoyl.

Heterocyclyl bonded via a ring carbon or ring nitrogen atom contains generally from 4 to 8, in particular from 5 to 7, ring atoms, and may have 1 or 2 fused-on phenyl or cycloalkyl radicals, or else be present as a spiro compound. Examples include pyrrolidino, piperidino, piperazino, morpholino, thiomorpholino, tetrahydrofuranyl, furanyl, pyranyl, tetrahydropyranyl, thiazolyl, oxazolyl, imidazolyl, indolinyl, isoindolinyl, 2,3-dihydrobenzimidazolyl, 1,2,3,4-tetrahydroquinolyl, 1,2,3,4-tetrahydroisoquinolyl, 1,2,3,4-tetrahydro-1,3-benzodiazinyl, 1,2,3,4-tetrahydro-1,4-benzodiazinyl, 3,4-dihydro-2H-1,4-benzoxazinyl, 3,4-dihydro-2H-1,4-benzothiazinyl, 3,4-dihydro-2H-1,3-benzothiazinyl, 3,4,5,6,7,8-hexahydro-2H-1,4-benzoxazinyl, 3,4,5,6,7,8-hexahydro-2H-1,4-benzothiazinyl, 2,3,4,5-tetrahydro-1H-1-benz[6,7-b]azepinyl and 5,6-dihydrophenanthridinyl. The radicals mentioned may be unsubstituted or N-substituted and/or C-substituted, in which case in particular 1, 2 or 3 substituents may be present.

Aryl contains generally 6-14, preferably 6-10 carbon atoms and is, for example, phenyl, indenyl, e.g. 2- or 4-indenyl, or naphthyl, e.g. 1- or 2-naphthyl. Preference is given to aryl having 6-10 carbon atoms, in particular phenyl or 1- or 2-naphthyl. The radicals mentioned may be unsubstituted or mono- or polysubstituted, e.g. mono- or disubstituted, for example by $C_1$-$C_8$-alkyl, cyano, hydroxyl, amino, $C_{1-6}$-alkylamino, di-$C_{1-6}$-alkylamino, $C_{2-6}$-alkenyl, $C_{2-6}$-alkynyl, $C_{0-6}$-alkylcarbonylamino, $C_{1-8}$-alkoxycarbonylamino, halogen, oxo, trifluoromethyl, $C_1$-$C_8$-alkoxy, optionally N-mono- or N-di-$C_1$-$C_8$-alkylcarbamoyl, $C_1$-$C_8$-alkoxycarbonyl, $C_{1-6}$-alkylenedioxy, aryl or heterocyclyl, and the substituents may be in any position, for example in the o-, m- or p-position of the phenyl radical, or in the 3- or 4-position of the 1- or 2-naphthyl radical, and a plurality of identical or different substituents may also be present.

Useful substituents of phenyl, phenyl(lower alkoxy), pyridyl(lower alkyl), pyridyl(lower alkoxy) and optionally hydrogenated and/or oxo-substituted heteroaryl or heterocyclyl include, for example, lower alkyl, lower alkoxy, hydroxyl, cyano, oxide, oxo, nitro, amino, (lower alkyl)amino, di(lower alkyl)amino, halogen, optionally N-mono- or N-di-$C_1$-$C_8$-alkylcarbamoyl, $C_1$-$C_8$-alkoxycarbonyl, $C_{1-6}$-alkylenedioxy and trifluoromethyl, and up to 3, in particular 1 or 2, identical or different substituents of those mentioned may be present.

Optionally hydrogenated and/or oxo-substituted heteroaryl radicals are, for example, optionally partially hydrogenated and/or benzofused 5-membered aza-, diaza-, triaza-, oxadiaza- or tetraazaaryl or 6-membered aza- or diazaaryl radicals, such as optionally oxo-substituted pyrrolidinyl, e.g. pyrrolidinyl or oxopyrrolidinyl, imidazolyl, e.g. imidazol-4-yl, benzimidazolyl, e.g. benzimidazol-2-yl, oxadiazolyl, e.g. 1,2,4-oxadiazol-5-yl, pyridyl, e.g. pyridin-2-yl, oxopiperidinyl, dioxopiperidinyl, oxothiazolyl, oxooxazolinyl or quinolinyl, e.g. quinolin-2-yl, or optionally N-(lower alkanoyl)ated piperidyl, such as 1-(lower alkanoyl)-piperidinyl.

Lower alkyl substituted by a heteroaryl radical which is bonded via a carbon atom and is optionally hydrogenated and/or oxo-substituted has, as the optionally hydrogenated heteroaryl radical, for example, an optionally partially hydrogenated and/or benzofused 5-membered aza-, diaza-, triaza-, oxadiaza- or tetraazaaryl radical, or 6-membered aza- or diazaaryl radical, and is, for example, optionally oxo-substituted pyrrolidinyl(lower alkyl), e.g. pyrrolidinyl(lower alkyl) or oxopyrrolidinyl(lower alkyl), imidazolyl(lower alkyl), benzimidazolyl(lower alkyl), oxadiazolyl(lower alkyl), pyridyl(lower alkyl), oxopiperidinyl(lower alkyl), dioxopiperidinyl (lower alkyl), oxothiazolyl(lower alkyl), oxooxazolinyl (lower alkyl) or quinolinyl(lower alkyl), and equally morpholinocarbonyl(lower alkyl) or optionally N-(lower alkanoyl)ated piperidyl(lower alkyl), such as 1-(lower alkanoyl)piperidinyl(lower alkyl).

Lower alkyl, for example $C_1$-$C_8$-alkyl, may be straight-chain or branched and is, for example, methyl, ethyl, propyl, isopropyl, butyl, isobutyl, sec-butyl, tert-butyl, or a pentyl, hexyl or heptyl group.

Lower alkenyl, for example $C_2$-$C_8$-alkenyl, may be straight-chain or branched and is, for example, vinyl, allyl, propenyl, isopropenyl, butenyl, isobutenyl or a pentenyl, hexenyl or heptenyl group.

Lower alkynyl, for example $C_2$-$C_6$-alkynyl, may be straight-chain or branched and is, for example, ethynyl, 1-propynyl, 3-propynyl, 1-butynyl, 3-butynyl, 4-butynyl, or a pentynyl or hexynyl group.

$C_{1-6}$-Alkylenedioxy is, for example, methylenedioxy, ethylenedioxy, 1,3-propylenedioxy or 1,2-propylenedioxy.

Amino(lower alkoxy) is, for example, amino-$C_1$-$C_4$-alkoxy, such as 2-aminoethoxy, 3-amino-propyloxy, 4-aminobutyloxy or 5-aminopentyloxy.

Aryl-$C_1$-$C_8$-alkanoyl is one of the aryl radicals mentioned which is bonded to the rest of the compound via a $C_1$-$C_8$-alkanoyl group, for example phenylformyl, phenylacetyl, 3-phenyl-propionyl, 2-phenyl-2-methylpropionyl or phenylpivaloyl.

Aryl-$C_0$-$C_4$-alkyl is one of the aryl radicals mentioned which is bonded to the rest of the compound either directly or a via a $C_1$-$C_4$-alkyl group.

Aryl-$C_3$-$C_8$-cycloalkanoyl is one of the aryl radicals mentioned which is bonded to the rest of the compound via a $C_3$-$C_8$-cycloalkanoyl group, for example 1-phenylcyclobutanoyl.

Carbamoyl(lower alkoxy) is, for example, carbamoyl-$C_1$-$C_8$-alkoxy, such as carbamoyl-methoxy, 2-carbamoylethoxy, 3-carbamoylpropyloxy 2-(3-carbamoyl)propyloxy, 2-carbamoyl-propyloxy, 3-(1-carbamoyl)propyloxy, 2-(2-carbamoyl)propyloxy, 2-(carbamoyl-2-methyl)-propyloxy, 4-carbamoylbutyloxy, 1-carbamoylbutyloxy, 1-(1-carbamoyl-2-methyl)butyloxy, 3-(4-carbamoyl-2-methyl)butyloxy, in particular 3-carbamoylpropyloxy or 2-carbamoyl-2-methylethoxy.

Carbamoyl(lower alkyl) is, for example, carbamoyl-$C_1$-$C_8$-alkyl, such as carbamoyl-methyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoyl-butyl, 1-carbamoylbutyl, 1-(1-carbamoyl-2-methyl)butyl, 3-(4-carbamoyl-2-methyl)butyl, in particular 3-carbamoylpropyl or 2-carbamoyl-2-methylethyl.

Carboxy(lower alkoxy) is, for example, carboxy-$C_1$-$C_4$-alkoxy, such as carboxymethoxy, 2-carboxyethoxy, 2- or 3-carboxypropyloxy 2-carboxy-2-methylpropyloxy, 2-carboxy-2-ethyl-butyloxy or 4-carboxybutyloxy, in particular carboxymethoxy.

Cycloalkoxy has, for example, from 3 to 8, in particular from 5 to 7 ring members, and is, for example, cyclopentyloxy, cyclohexyloxy or cycloheptyloxy, and also cyclopropyloxy, cyclobutyloxy or cyclooctyloxy.

Cycloalkyl has, for example, from 3 to 12, in particular from 5 to 10 ring members, and is, for example, cyclopentyl, cyclohexyl or cycloheptyl, and also cyclopropyl, cyclobutyl, cyclooctyl or adamantyl.

$C_3$-$C_{12}$-Cycloalkyl-$C_3$-$C_8$-cycloalkanoyl is one of the cycloalkyl radicals mentioned which is bonded to the rest of the compound via a $C_3$-$C_8$-Cycloalkanoyl group, for example 1-cyclohexylcyclobutanoyl.

$C_3$-$C_{12}$-Cycloalkyl-$C_1$-$C_8$-alkanoyl is one of the cycloalkyl radicals mentioned which is bonded to the rest of the compound via a $C_1$-$C_8$-alkanoyl group, for example adamantylformyl, cyclobutylformyl, cyclopentylformyl, cyclohexylformyl, cyclohexylacetyl, 2-cyclopentyl-2-methylpropionyl, 2-cyclohexylpropionyl, 3-cyclohexylpropionyl or 2-cyclohexyl-2-methyl-propionyl.

Di(lower alkyl)amino(lower alkoxy) is, for example, N,N-di-$C_1$-$C_4$-alkylamino-$C_1$-$C_4$-alkoxy, such as 2-dimethylaminoethoxy, 3-dimethylaminopropyloxy, 4-dimethylaminobutyloxy, 2-diethylaminoethoxy, 2-(N-methyl-N-ethylamino)ethoxy or 2-(N-butyl-N-methylamino)ethoxy, in particular 3-dimethylaminopropyloxy.

Di(lower alkyl)amino(lower alkyl) is, for example, N,N-di-$C_1$-$C_4$-alkylamino-$C_1$-$C_4$-alkyl, such as 2-dimethylaminoethyl, 3-dimethylaminopropyl, 4-dimethylaminobutyl, 2-diethylaminoethyl, 2-(N-methyl-N-ethylamino)ethyl or 2-(N-butyl-N-methylamino)ethyl, in particular dimethylaminomethyl.

Di(lower alkyl)amino is, for example, di-$C_1$-$C_4$-alkylamino, such as dimethylamino, N-methyl-N-ethylamino, diethylamino, N-methyl-N-propylamino or N-butyl-N-methylamino.

Di(lower alkyl)amino(lower alkoxy) is, for example, N,N-di-$C_1$-$C_4$-alkylamino-$C_1$-$C_4$-alkoxy, such as 2-dimethylaminoethoxy, 3-dimethylaminopropyloxy, 2-dimethylaminopropyloxy, 2-(dimethylamino-2-methyl)propyloxy or 2-(1-dimethylamino-3-methyl)butyloxy, in particular 3-dimethylaminopropyloxy.

Di(lower alkyl)carbamoyl is, for example, di-$C_1$-$C_4$-alkylcarbamoyl, such as dimethyl-carbamoyl, N-methyl-N-ethylcarbamoyl, diethylcarbamoyl, N-methyl-N-propylcarbamoyl or N-butyl-N-methylcarbamoyl.

Di(lower alkyl)carbamoyl(lower alkyl) is, for example, N,N-di-$C_1$-$C_4$-alkylcarbamoyl-$C_1$-$C_4$-alkyl, such as 2-dimethylcarbamoylethyl, 3-dimethylcarbamoylpropyl, 2-dimethylcarbamoyl-propyl, 2-(dimethylcarbamoyl-2-methyl)propyl or 2-(1-dimethylcarbamoyl-3-methyl)butyl, in particular 2-dimethylcarbamoylethyl.

Halogen is, for example, fluorine, chlorine, bromine or iodine, preferably fluorine and chlorine.

Heterocyclyl-$C_0$-$C_4$-alkyl is one of the heterocyclyl radicals mentioned which is bonded to the rest of the compound either directly or via a $C_1$-$C_4$-alkyl group.

Morpholino(lower alkoxy) is, for example, morpholino-$C_1$-$C_4$-alkoxy, such as morpholino-methoxy, 2-morpholinoethoxy, 3-morpholinopropyloxy or 4-morpholinobutyloxy, in particular 2-morpholinoethoxy or 3-morpholinopropyloxy.

Morpholino(lower alkyl) is, for example, morpholino-$C_1$-$C_4$-alkyl, such as morpholinomethyl, 2-morpholinoethyl, 3-morpholinopropyl or 4-morpholinobutyl, in particular morpholinomethyl, 2-morpholinoethyl or 3-morpholinopropyl.

Morpholino(lower alkyl)carbamoyl(lower alkoxy) is, for example, N-(morpholino-$C_1$-$C_4$-alkyl-carbamoyl)-$C_1$-$C_4$-alkoxy, in particular 2-morpholinoethylcarbamoylmethoxy.

Lower alkanoyl is, for example, $C_1$-$C_8$-alkanoyl, such as formyl, acetyl or pivaloyl.

(Lower alkanoyl)piperazino(lower alkyl) is, for example, N'—$C_2$-$C_8$-(lower alkanoyl)piperazino-$C_1$-$C_4$-alkyl, such as 4-acetylpiperazinomethyl.

Lower alkoxy is, for example, $C_1$-$C_8$-alkoxy, preferably $C_1$-$C_4$-alkoxy, such as methoxy, ethoxy, propyloxy, isopropyloxy, butyloxy, isobutyloxy, sec-butyloxy, tert-butyloxy, pentyloxy, or a hexyloxy or heptyloxy group.

Lower alkoxycarbonyl is, for example, $C_1$-$C_4$-alkoxycarbonyl, such as methoxycarbonyl, ethoxycarbonyl, propyloxycarbonyl, isopropyloxycarbonyl, butyloxycarbonyl, isobutyloxy-carbonyl, sec-butyloxycarbonyl, tert-butyloxycarbonyl, pentyloxycarbonyl, or a hexyloxycarbonyl or heptyloxycarbonyl group.

(Lower alkoxy)(lower alkoxy) is, for example, $C_1$-$C_4$-alkoxy-$C_2$-$C_4$-alkoxy, such as 2-methoxy-, 2-ethoxy- or 2-propyloxyethoxy, 3-methoxy- or 3-ethoxypropyloxy or 4-methoxybutyloxy, in particular 2-methoxyethoxy, 3-methoxypropyloxy, 4-methoxybutyloxy, 5-methoxypentyloxy.

(Lower alkoxy)(lower alkoxy)(lower alkoxy) is, for example, $C_1$-$C_4$-alkoxy-$C_1$-$C_4$-alkoxy-$C_1$-$C_4$-alkoxy; such as 2-methoxy-, 2-ethoxy- or 2-propyloxyethoxymethoxy, 2-(2-methoxy-, 2-ethoxy- or 2-propyloxyethoxy)ethoxy, 3-(3-methoxy- or 3-ethoxypropyloxy)propyloxy or 4-(2-methoxybutyloxy)butyloxy, in particular 2-(methoxymethoxy)ethoxy or 2-(2-methoxy-ethoxy)ethoxy.

(Lower alkoxy)(lower alkyl) is, for example, $C_1$-$C_4$-alkoxy-$C_1$-$C_4$-alkyl, such as ethoxymethyl, propyloxymethyl, butyloxymethyl, 2-methoxy-, 2-ethoxy- or 2-propyloxyethyl, 3-methoxy- or 3-ethoxypropyl or 4-methoxybutyl, in particular 3-methoxypropyl or 4-methoxybutyl, in particular propyloxymethyl.

Lower alkyl may be straight-chain or branched and/or bridged and is, for example, corresponding $C_1$-$C_8$-alkyl, such as methyl, ethyl, propyl, isopropyl, butyl, isobutyl, seobutyl, tert-butyl, or a pentyl, hexyl, heptyl or octyl group.

(Lower alkyl)amino is, for example, $C_1$-$C_4$-alkylamino, such as methylamino, ethylamino, propylamino, butylamino, isobutylamino, sec-butylamino or tert-butylamino.

(Lower alkyl)carbamoyl is, for example, $C_1$-$C_4$-alkylcarbamoyl, such as methylcarbamoyl, ethylcarbamoyl, propylcarbamoyl, butylcarbamoyl, isobutylcarbamoyl, sec-butylcarbamoyl or tert-butylcarbamoyl, in particular methylcarbamoyl.

(Lower alkyl)carbamoyl(lower alkoxy) is, for example, N—$C_1$-$C_4$-alkylcarbamoyl-$C_1$-$C_4$-alkoxy, such as 2-propylcarbamoylethoxy, 3-ethylcarbamoylpropyloxy, 2-ethylcarbamoylpropyloxy, 2-(methylcarbamoyl-2-methyl)propyloxy, 2-(1-methylcarbamoyl-3-methyl)butyloxy or in particular butylcarbamoylmethoxy.

(Lower alkyl)carbamoyl(lower alkyl) is, for example, N—$C_1$-$C_8$-alkylcarbamoyl-$C_1$-$C_4$-alkyl, such as methyl- or dimethylcarbamoyl-$C_1$-$C_4$-alkyl, e.g. methylcarbamoylmethyl, 2-methyl-carbamoylethyl, 3-methylcarbamoylpropyl or in particular 2-methylcarbamoyl-2-methylpropyl.

(Lower alkyl)piperazino(lower alkyl) is, for example, N'—$C_1$-$C_4$-alkylpiperazino-$C_1$-$C_4$-alkyl, such as N'-methylpiperazinomethyl, 2-(N'-methylpiperazino)ethyl, 3-(N'-methylpiperazino)-propyl or 4-(N'-methylpiperazino)butyl, in particular N'-methylpiperazinomethyl.

Piperidino(lower alkoxy) is, for example, piperidino-$C_1$-$C_4$-alkoxy, such as 2-piperidinoethoxy, 3-piperidinopropyloxy or 4-piperidinobutyloxy, in particular 2-piperidinoethoxy.

Piperidino(lower alkyl) is, for example, piperidino-$C_1$-$C_4$-alkyl, such as piperidinomethyl, 2-piperidinoethyl, 3-piperidinopropyl or 4-piperidinobutyl, in particular piperidinomethyl.

Pyrrolidino(lower alkyl) is, for example, pyrrolidino-$C_1$-$C_4$-alkyl, such as pyrrolidinomethyl, 2-pyrrolidinoethyl, 3-pyrrolidinopropyl or 4-pyrrolidinobutyl, in particular pyrrolidinomethyl.

$C_1$-$C_8$-Alkylsulphonyl is, for example, methylsulphonyl, ethylsulphonyl, propylsulphonyl, isopropylsulphonyl, butylsulphonyl, isobutylsulphonyl, sec-butylsulphonyl, tert-butylsulphonyl, or a pentyl, hexyl, heptyl or octylsulphonyl group.

$C_3$-$C_8$-Cycloalkylsulphonyl is, for example, cyclopentylsulphonyl, cyclohexylsulphonyl or cycloheptylsulphonyl, and also cyclopropylsulphonyl, cyclobutylsulphonyl or cyclooctylsulphonyl.

Aryl-$C_0$-$C_8$-alkylsulphonyl is one of the aryl radicals mentioned which is bonded to the rest of the compound either via a sulphonyl group or via a $C_1$-$C_8$-alkylsulphonyl group, for example phenylsulphonyl, benzylsulphonyl or phenyldimethylenesulphonyl.

Heterocyclylsulphonyl is one of the heterocyclyl radicals mentioned which is bonded to the rest of the compound via a sulphonyl group.

Depending on the presence of asymmetric carbon atoms, the inventive compounds may be present in the form of isomer mixtures, especially as racemates, or in the form of pure isomers, especially of optical antipodes.

Salts of compounds having salt-forming groups are in particular acid addition salts, salts with bases, or, in the presence of a plurality of salt-forming groups, in some cases also mixed salts or internal salts.

Salts are primarily the pharmaceutically usable or nontoxic salts of compounds of the formula I.

Such salts are formed, for example, from compounds of the formula I with an acidic group, for example a carboxyl or sulpho group, and are, for example, the salts thereof with suitable bases such as non-toxic metal salts derived from metals of group Ia, Ib, IIa and IIb of the Periodic Table of the Elements, for example alkali metal, in particular lithium, sodium, or potassium, salts, alkaline earth metal salts, for example magnesium or calcium salts, and also zinc salts and ammonium salts, including those salts which are formed with organic amines, such as optionally hydroxy-substituted mono-, di- or trialkylamines, in particular mono-, di- or tri(lower alkyl)amines, or with quaternary ammonium bases, e.g. methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amine, such as N,N-di-N-dimethyl-N-(2-hydroxy-ethyl)amine, or N-methyl-D-glucamine, or quaternary ammonium hydroxides such as tetrabutylammonium hydroxide. The compounds of the formula I having a basic group, for example an amino group, may form acid addition salts, for example with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic, sulpho or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the alpha-amino acids mentioned above, and also methanesulphonic acid, ethanesulphonic acid, 2-hydroxyethanesulphonic acid, ethane-1,2-disulphonic acid, benzenesulphonic acid, 4-methylbenzenesulphonic acid, naphthalene-2-sulphonic acid, 2- or 3-phosphoglycerate, glucose 6-phosphate, N-cyclohexylsulphamic acid (with formation of the cyclamates) or with other acidic organic compounds such as ascorbic acid. Compounds of the formula I having acidic and basic groups may also form internal salts.

For the isolation and purification, pharmaceutically unsuitable salts may also find use.

The compound groups mentioned hereinbelow are not to be regarded as closed, but rather it is possible in a sensible manner, for example, to replace general by more specific definitions by exchanging parts of these compound groups with one another or with the definitions given above, or omitting them.

The invention relates primarily to compounds of the formula I, in particular of the formula Ia

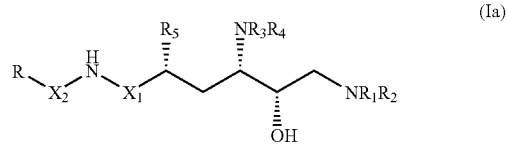

(Ia)

where $R_1$ is a) hydrogen; or
is b) $C_1$-$C_8$-alkyl or $C_3$-$C_8$-cycloalkyl;

$R_2$ is a) $C_1$-$C_8$-alkyl, $C_3$-$C_8$-cycloalkyl, $C_1$-$C_8$-alkanoyl, heterocyclyl-$C_1$-$C_8$-alkanoyl, $C_3$-$C_{12}$-cycloalkyl-$C_1$-$C_8$-alkanoyl or aryl-$C_1$-$C_8$-alkanoyl, which radicals may be substituted by 1-4 $C_1$-$C_8$-alkyl, $C_3$-$C_8$-cycloalkyl, $C_3$-$C_8$-cycloalkoxy, $C_{1-6}$-alkylamino, cyano, halogen, hydroxyl, oxide, $C_0$-$C_6$-alkylcarbonylamino, $C_1$-$C_6$-alkoxycarbonylamino, $C_1$-$C_8$-alkoxy, oxo, trifluoromethyl or aryl; or
is b) together with $R_1$ and the nitrogen atom to which they are bonded, a saturated or partly unsaturated, 4-8-membered, heterocyclic ring which may contain an additional nitrogen or oxygen atom, in which case the additional nitrogen atom may optionally be substituted by $C_1$-$C_8$-alkyl or $C_1$-$C_8$-alkanoyl, and this heterocyclic ring may be part of a bicyclic or tricyclic ring system having a total of up to 16 members and the second ring may also contain a nitrogen or oxygen atom, and the nitrogen atom of the second ring may optionally be substituted by $C_1$-$C_8$-alkyl or $C_1$-$C_8$-alkanoyl, and all ring systems mentioned may be substituted by 1-4 $C_1$-$C_8$-alkyl, hydroxyl, oxo, oxide, $C_1$-$C_8$-alkoxy, $C_1$-$C_8$-alkoxy-$C_1$-$C_8$-alkoxy, $C_1$-$C_8$-alkylcarbonylamino or aryloxy-$C_0$-$C_4$-alkyl-$C_1$-$C_8$-alkoxy;

$R_3$ and $R_4$ are each hydrogen, $R_5$ is $C_1$-$C_4$-alkyl, such as methyl or isopropyl, R is a 2-$R_A$-4-$R_C$-phenyl radical, 2-$R_A$-pyridin-3-yl radical or 3-$R_A$-pyridin-2-yl radical, where $R_A$ is $C_1$-$C_4$-alkoxy-$C_1$-$C_4$-alkyl such as propyloxymethyl, morpholino-$C_1$-$C_4$-alkyl such as 2-morpholinoethyl or 3-morpholinopropyl, $C_1$-$C_8$-alkanoylpiperazino-$C_1$-$C_4$-alkyl such as N'-acetylpiperazinomethyl, $C_1$-$C_8$-alkoxy such as propyloxy, $C_1$-$C_4$-alkoxy-$C_1$-$C_5$-alkoxy such as 2-methoxyethoxy, 3-methoxypropyloxy, 4-methoxy-butyloxy or 5-methoxypentyloxy, $C_1$-$C_4$-alkoxy-$C_2$-$C_4$-alkenyloxy such as 4-methoxy-but-2-enyloxy, $C_1$-$C_4$-alkoxy-$C_1$-$C_4$-alkoxy-$C_1$-$C_4$-alkoxy such as 2-(methoxy-methoxy)ethoxy or 2-(2-methoxy-ethoxy)ethoxy, amino-$C_1$-$C_4$-alkoxy such as 2-aminoethoxy or 3-aminopropyloxy, di-$C_1$-$C_4$-alkylamino-$C_1$-$C_4$-alkoxy such as 3-dimethylaminopropyloxy, $C_1$-$C_8$-alkanoyl-amino-$C_1$-$C_4$-alkoxy such as N-acetylaminoethoxy, $C_1$-$C_8$-alkanoyl-amino-$C_1$-$C_4$-alkyl such as N-acetylaminoethyl, carbamoyl-$C_1$-$C_4$-alkoxy such as 2-carbamoylethoxy or carbamoyl, and $R_C$ is hydrogen, di-$C_1$-$C_4$-alkylamino-$C_1$-$C_4$-alkyl such as dimethylaminomethyl, piperidino-$C_1$-$C_4$-alkyl such as piperidinomethyl, pyrrolidino-$C_1$-$C_4$-alkyl such as pyrrolidinomethyl, morpholino-$C_1$-$C_4$-alkyl such as morpholinomethyl, $C_1$-$C_8$-alkanoylpiperazino-$C_1$-$C_4$-alkyl such as N'-acetylpiperazinomethyl, or $C_1$-$C_4$-alkylpiperazino-$C_1$-$C_4$-alkyl such as N'-methylpiperazinomethyl, morpholino, $C_1$-$C_4$-alkoxy such as methoxy, morpholino-$C_1$-$C_4$-alkoxy such as 2-morpholinoethoxy or 3-morpholinopropylox, morpholino-$C_1$-$C_4$-alkylcarbamoyl-$C_1$-$C_4$-alkoxy such as 2-morpholinoethylcarbamoylmethoxy, piperidino-$C_1$-$C_4$-alkoxy such as 2-piperidino-ethoxy, carboxyl, carbamoyl, $C_1$-$C_4$-alkylcarbamoyl such as methylcarbamoyl, carboxy-$C_1$-$C_4$-alkoxy such as carboxymethoxy, di-$C_1$-$C_4$-alkylamino-$C_1$-$C_4$-alkoxy, such as 3-dimethylaminopropyloxy, $C_1$-$C_8$-alkylcarbamoyl-$C_1$-$C_4$-alkoxy such as butylcarbamoylmethoxy, or tetrazolyl-$C_1$-$C_4$-alkoxy, such as tetrazol-5-ylmethoxy, $X_1$ is methylene and $X_2$ is carbonyl, and salts thereof, in particular pharmaceutically usable salts thereof.

The invention relates specifically to the compounds of the formula I specified in the examples and salts thereof, in particular the pharmaceutically usable salts thereof.

Salts obtained may be converted to other salts in a manner known per se, acid addition salts, for example, by treating with a suitable metal salt such as a sodium, barium or silver salt, of another acid in a suitable solvent in which an inorganic salt which forms is insoluble and thus separates out of the reaction equilibrium, and base salts by release of the free acid and salt reformation.

The compounds of the formula I, including their salts, may also be obtained in the form of hydrates or include the solvent used for the crystallization.

Owing to the narrow relationship between the novel compounds in free form and in the form of their salts, the free compounds and salts thereof refer above and below analogously and appropriately, where appropriate, also to the corresponding salts and free compounds thereof respectively.

Stereoisomer mixtures, i.e. mixtures of diastereomers and/or enantiomers, for example racemic mixtures, may be separated into the corresponding isomers in a manner known per se by suitable separation processes. For instance, diastereomer mixtures may be separated into the individual diastereomers by fractional crystallization, chromatography, solvent partition, etc. After conversion of the optical antipodes to diastereomers, for example by reacting with optically active compounds, e.g. optically active acids or bases, racemates may be separated from one another by chromatography on column materials laden with optically active compounds or by enzymatic methods, for example by selective conversion of only one of the two enantiomers. This separation may be effected either at the stage of one of the starting materials or on the compounds of the formula I. It is possible for the configuration at individual chiral centres in a compound of the formula I to be inverted selectively.

For example, the configuration of asymmetric carbon atoms which bear nucleophilic substituents, such as amino or hydroxyl, may be inverted by second-order nucleophilic substitution, if appropriate after conversion of the bonded nucleophilic substituent to a suitable nudeofugic leaving group and reaction with a reagent which introduces the original substituents, or the configuration at carbon atoms having hydroxyl groups can be inverted by oxidation and reduction, analogously to the process in the European patent application EP-A-0 236 734.

Also advantageous is the reactive functional modification of the hydroxyl group and subsequent replacement thereof by hydroxyl with inversion of configuration. To this end, the amino and hydroxyl group drawn in formula I are bridged by a bivalent group, in particular carbonyl, to obtain a compound which can be cleaved again on treatment with thionyl chloride with inversion of configuration.

The compounds of the formula (I) may be prepared in an analogous manner to the preparation processes known from the literature. The starting materials for carrying out the preparation processes are described, for example, in EP 07 16077. The inventive compounds of the formula I and salts of such compounds having at least one salt-forming group are obtained by processes known per se, for example, by a) condensing a compound of the formula II

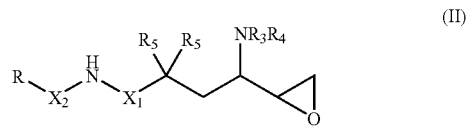

where R, $R_3$, $R_4$, $R_5$, $X_1$ and $X_2$ are each as defined above or a salt thereof with a compound of the formula $R_1R_2NH$ (III) where $R_1$ and $R_2$ are each as defined above, in the course of which free functional groups present in the reaction components with the exception of the groups taking part in the reaction are present in protected form, and detaching protecting groups present. In cases where $R_1$ and $R_2$ are a saturated or partly unsaturated oxo-substituted heterocyclic ring (for example lactams) and strong bases are used as a reagent, the alkoxide formed by epoxide opening may react with one of the protecting groups present (e.g. N-Boc) and form an oxazolidinone which can be cleaved, for example, with lithium hydroxide to give the product or b) condensing a compound of the formula II

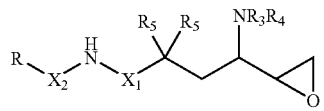
(II)

where R, $R_3$, $R_4$, $R_5$, $X_1$ and $X_2$ are each as defined above or a salt thereof with an azide, reducing the azido group to amino and then, depending on the definitions of $R_1$ and $R_2$, mono- or dialkylating, mono- or diacylating, and optionally sulphonylating the amino group, in the course of which free functional groups present in the reaction components with the exception of the groups taking part in the reaction are present in protected form, and detaching protecting groups present or c) condensing a compound of the formula IV

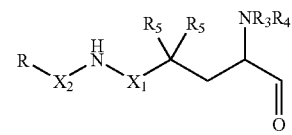
(IV)

where R, $R_3$, $R_4$, $R_5$, $X_1$ and $X_2$ are each as defined above or a salt thereof with cyanide or nitromethane, reducing the nitrile group or nitro group to amino and then, depending on the definitions of $R_1$ and $R_2$, mono- or dialkylating, mono- or diacylating, and optionally sulphonylating the amino group, in the course of which free functional groups present in the reaction components with the exception of the groups taking part in the reaction are present in protected form, and detaching protecting groups present.

It is possible to prepare compounds of the formula II in an analogous manner to preparation processes known from the literature, for example by a) condensing a compound of the formula IV

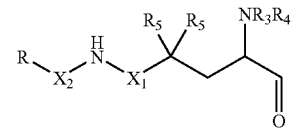
(IV)

where R, $R_3$, $R_4$, $R_5$, $X_1$ and $X_2$ are each as defined above or a salt thereof with methylide (see, for example, in Tet. Lett. 30(40), 5425-5428, 1989), in the course of which free functional groups present in the reaction components with the exception of the groups taking part in the reaction are present in protected form, and detaching protecting groups present, or b) epoxidizing a compound of the formula V

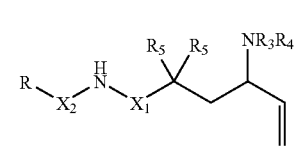
(V)

where R, $R_3$, $R_4$, $R_5$, $X_1$ and $X_2$ are each as defined above or a salt thereof (see, for example, in J. Med. Chem. 35(10), 1685-1701, 1992 and J. Org. Chem. 59(3), 653-657, 1994), in the course of which free functional groups present in the reaction components with the exception of the groups taking part in the reaction are present in protected form, and detaching protecting groups present, or c) dihydroxylating a compound of the formula V

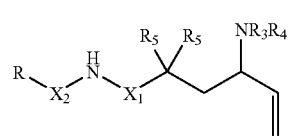
(V)

where R, $R_3$, $R_4$, $R_5$, $X_1$ and $X_2$ are each as defined above or a salt thereof, tosylating the primary alcohol and subsequently admixing with a base such as potassium hydroxide (see, for example, in WO 03050073), in the course of which free functional groups present in the reaction components with the exception of the groups taking part in the reaction are present in protected form, and detaching protecting groups present, or d) preparing an activated ester from a compound of the formula VI

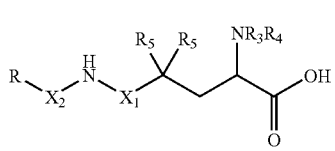
(VI)

where R, $R_3$, $R_4$, $R_5$, $X_1$ and $X_2$ are each as defined above or a salt thereof, and admixing it with diazomethane, admixing the diazoketone with 48% HBr, and then reducing the bromoketone and subsequently admixing with a base such as potassium hydroxide (see, for example, in WO 03050073), in the course of which free functional groups present in the reaction components with the exception of the groups taking part in the reaction are present in protected form, and detaching protecting groups present.

Details of specific preparation variants can be taken from the examples.

The compounds of the formula (I) may also be prepared in optically pure form. The separation into antipodes may be effected by methods known per se, either preferably at a synthetically early stage by salt formation with an optically active acid, for example (+)- or (−)-mandelic acid, and separation of the diastereomeric salts by fractional crystallization, or preferably at a rather later stage by derivatization with a chiral auxiliary building block, for example (+)- or (−)-camphanoyl chloride, and separation of the diastereomeric products by chromatography and/or crystallization and subsequent cleavage of the bond to the chiral auxiliary. The pure diastereomeric salts and derivatives may be analysed with common spectroscopic methods to determine the absolute configuration of the piperidine present, and X-ray spectroscopy on single crystals constitutes a particularly suitable method.

Prodrug derivatives of the compounds described in the present context are derivatives thereof which, on in vivo application, release the original compound by a chemical or physiological process. A prodrug may be converted to the original compound, for example, when a physiological pH is attained or by enzymatic conversion. Prodrug derivatives may, for example, be esters of freely available carboxylic acids, S- and O-acyl derivatives of thiols, alcohols or phenols, and the acyl group is as defined in the present context. Preference is given to pharmaceutically usable ester derivatives which are converted by solvolysis in physiological medium to the original carboxylic acid, for example lower alkyl esters, cycloalkyl esters, lower alkenyl esters, benzyl esters, mono- or disubstituted lower alkyl esters such as lower ω-(amino, mono- or dialkylamino, carboxyl, lower alkoxycarbonyl)-alkyl esters or such as lower α-(alkanoyloxy, alkoxycarbonyl or dialkylaminocarbonyl)-alkyl esters; as such, pivaloyloxymethyl esters and similar esters are utilized in a conventional manner.

Owing to the close relationship between a free compound, a prodrug derivative and a salt compound, a certain compound in this invention also encompasses its prodrug derivative and salt form, where these are possible and appropriate.

The compounds of the formula (I) also include those compounds in which one or more atoms are replaced by their stable, non-radioactive isotopes; for example, a hydrogen atom by deuterium.

The compounds of the formula (I) and their pharmaceutically usable salts have inhibiting action on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II increases the blood pressure both directly by arterial constriction and indirectly by the hormone aldosterone which inhibits the release of the sodium ion from the adrenal glands, which is associated with a rise in the extracellular liquid volume. This rise can be attributed to the action of angiotensin II itself or of the heptapeptide angiotensin III formed therefrom as a cleavage product. Inhibitors of the enzymatic activity of renin bring about a reduction in the formation of angiotensin I and, as a consequence thereof, the formation of a smaller amount of angiotensin II. The reduced concentration of this active peptide hormone is the immediate cause of the hypotensive action of renin inhibitors.

The action of renin inhibitors is detected experimentally with an in vitro test [Nussberger et al. (1987) J. Cardiovascular Pharmacol., Vol. 9, p. 39-44]. This test measures the formation of angiotensin I in human plasma. The amount of angiotensin I formed is determined in a subsequent radioimmunoassay. Which action inhibitors have on the formation of angiotensin I is tested in this system by the addition of different concentrations of these substances. The $IC_{50}$ refers to that concentration of the particular inhibitor which reduces the formation of angiotensin I by 50%. The compounds of the present invention exhibit inhibiting actions in the in vitro systems at minimum concentrations of about $10^{-6}$ to about $10^{-10}$ mol/l.

In salt-depleted animals, renin inhibitors bring about a blood pressure decrease. Human renin differs from renin of other species. To test inhibitors of human renin, primates (marmosets, Callithrixjacchus) are used, because human renin and primate renin are substantially homologous in the enzymatically active region. One in vivo test which is used is as follows: the test compounds are tested on normotensive marmosets of both genders and having a body weight of about 350 g which are conscious, able to move freely and in their normal cages. Blood pressure and heart rate are measured using a catheter in the descending aorta and recorded radiometrically. The endogenous release of renin is stimulated by the combination of a 1-week low-salt diet with a single intramuscular injection of furosemide (5-(aminosulphonyl)-4-chloro-2-[(2-furanylmethyliamino]benzoic acid) (5 mg/kg). 16 hours after the injection of furosemide, the test substances are administered either directly into the femoral artery by means of an injection cannula or into the stomach by gavage as a suspension or solution, and their effect on blood pressure and heart rate was evaluated. The compounds of the present invention effectively reduce blood pressure in the in vivo test described at doses of about 0.003 to about 0.3 mg/kg i.v. and at doses of about 0.3 to about 30 mg/kg p.o.

The compounds of the present invention may be used for the treatment of hypertension, congestive heart failure, cardiac hypertrophy, cardiac fibrosis, cardiomyopathy postinfarction, complications owing to diabetes such as nephropathy, vasculopathy and neuropathy, diseases of the cardiac vessels, restenosis after angioplasty, increased intraocular pressure, glaucoma, abnormal vascular growth, hyperaldosteronism, states of anxiety and cognitive disorders.

The compounds of the formula (I) and the pharmaceutically usable salts thereof may find use as medicines, for example in the form of pharmaceutical preparations. The pharmaceutical preparations may be administered enterally, such as orally, for example in the form of tablets, coated tablets, sugar-coated tablets, hard and soft gelatine capsules, solutions, emulsions or suspensions, nasally, for example in the form of nasal sprays, rectally, for example in the form of suppositories, or transdermally, for example in the form of ointments or patches. The administration may also be parenteral, such as intramuscular or intravenous, for example in the form of injection solutions.

To prepare tablets, coated tablets, sugar-coated tablets and hard gelatine capsules, the compounds of the formula (I) and pharmaceutically usable salts thereof may be processed with pharmaceutically inert, inorganic or organic excipients. Such excipients used, for example for tablets, coated tablets and hard gelatine capsules, may be lactose, corn starch, or derivatives thereof, talc, stearic acid or salts thereof etc.

Suitable excipients for soft gelatine capsules are, for example, vegetable oils, waxes, fats, semisolid and liquid polyols, etc.

Suitable excipients for preparing solutions and syrups are, for example, water, polyols, sucrose, invert sugar, glucose, etc.

Suitable excipients for injection solutions are, for example, water, alcohols, polyols, glycerol, vegetable oils, bile acids, lecithin, etc.

Suitable excipients for suppositories are, for example, natural or hardened oils, waxes, fats, semisolid or liquid polyols, etc.

The pharmaceutical preparations may additionally also comprise preservatives, solubilizers, viscosity-increasing substances, stabilizers, wetting agents, emulsifiers, sweeteners, colorants, flavourings, salts for altering the osmotic pressure, buffers, coatings or antioxidants. They may also comprise other therapeutically valuable substances.

The present invention further provides the use of the compounds of the formula (I) and the pharmaceutically usable salts thereof in the treatment or prevention of hypertension and heart failure, and also glaucoma, cardiac infarction, kidney failure and restenoses.

The compounds of the formula (I) and the pharmaceutically usable salts thereof may also be administered in combination with one or more agents having cardiovascular action, for example α- and β-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexilene, verapamil, gallopamil, nifedipine etc.; ACE inhibitors such as cilazapril, captopril, enalapril, lisinopril etc.; potassium activators such as pinacidil; anti-serotoninergics such as ketanserin; thromboxane-synthetase inhibitors; neutral endopeptidase inhibitors (NEP inhibitors); angiotensin II antagonists; and also diuretics such as hydrochlorothiazide, chlorothiazide, acetazolamide, amiloride, bumetanide, benzthiazide, ethacrynic acid, furosemide, indacrinone, metolazone, spironolactone, triamteren, chlorthalidone etc.; sympatholytics such as methyidopa, clonidine, guanabenz, reserpine; and other agents which are suitable for the treatment of hypertension, heart failure or vascular diseases in humans and animals which are associated with diabetes or renal disorders such as acute or chronic renal failure. Such combinations may be employed separately or in preparations which comprise a plurality of components.

Further substances which can be used in combination with the compounds of the formula (I) are the compounds of classes (i) to (ix) on page 1 of WO 02/40007 (and also the preferences and examples further listed therein) and the substances specified on pages 20 and 21 of WO 03/027091.

The dose may vary within wide limits and has of course to be adapted to the individual circumstances in each individual case. In general, for oral administration, a daily dose of about 3 mg to about 3 g, preferably about 10 mg to about 1 g, for example about 300 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

The examples which follow are intended to illustrate the present invention, but not to restrict it in any way. All temperatures are reported in degrees Celsius, pressures in mbar. Unless stated otherwise, the reactions take place at room temperature. The abbreviation "Rf=xx (A)" means, for example, that the Rf value xx is obtained in the solvent system A. The ratio of the solvents relative to one another is always reported in parts by volume. Chemical names of end products and intermediates were obtained with the aid of the program AutoNom 2000 (Automatic Nomenclature).

HPLC gradients on Hypersil BDS C-18 (5 μm); column: 4×125 mm

I 90% water*/10% acetonitrile*to 0% water*/100% acetonitrile*in 5 minutes+2.5 minutes (1.5 ml/min)

II 95% water*/5% acetonitrile*to 0% water*/100% acetonitrile*in 40 minutes (0.8 ml/min)

*: containing 0.1% trifluoroacetic acid

The following abbreviations are used:

Rf ratio of distance traveled by a substance to separation of the eluent front from the start point in thin layer chromatography Rt retention time of a substance in HPLC (in minutes)

m.p. melting point (temperature)

EXAMPLE 1

N-(4(S)-Amino-5(S)-hydroxy-2(S)-isopropyl-6-piperidin-1-ylhexyl)-2-(3-methoxypropoxy)-benzamide dihydrochloride

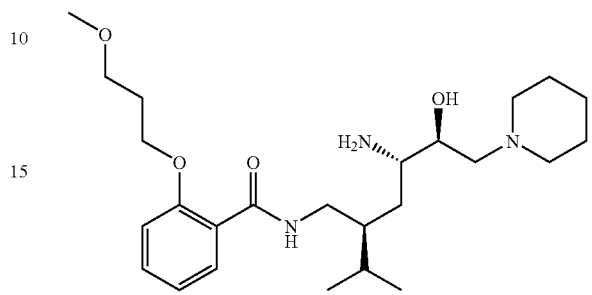

The solution of 0.024 g of tert-butyl (1(S)-(1(S)-hydroxy-2-piperidin-1-ylethyl)-3(S)-{[2-(3-methoxypropoxy)benzoylamino]methyl}-4-methylpentyl)carbamate in 1 ml of 4M HCl (in dioxane) is stirred at 0° C. over 3 hours and subsequently concentrated by evaporation to dryness—the residue is dissolved in 1 ml of tert-butanol, frozen and lyophilized under high vacuum. The title compound is obtained as a white powder. Rf=0.09 (200:20:1 dichloromethane-methanol-25% conc. ammonia); Rt=2.95 (gradient I).

The starting materials are prepared as follows:

a) tert-Butyl (1(S)-(1(S)-hydroxy-2-piperidin-1-ylethyl)-3(S)-{[2-(3-methoxypropoxy)-benzoylamino]methyl}-4-methylpentyl)carbamate A solution of 0.030 g of tert-butyl (3(S)-{[2-(3-methoxypropoxy)benzoylamino]methyl}-4-methyl-1(S)—(R)-oxiranylpentyl)carbamate in 0.60 ml of isopropanol and 0.050 ml of piperidine is stirred at 70° C. over 1 hour. The reaction mixture is concentrated by evaporation, and the residue is admixed with water and extracted with tert-butyl methyl ether (2×). The combined organic phases are washed with water and brine, dried over sodium sulphate and concentrated by evaporation. The title compound is obtained from the residue by means of flash chromatography (SiO2 60F) as a slightly yellowish oil. Rf=0.34 (200:20:1 dichloromethane-methanol-25% conc. ammonia); Rt=4.08 (gradient I).

b) tert-Butyl (3(S)-{[2-(3-methoxypropoxy)benzoylamino]methyl}-4-methyl-1(S)—(R)-oxiranylpentyl) carbamate The solution of 1.48 g of tert-butyl (3(S)-{[2-(3-methoxypropoxy)benzoylamino]methyl}-4-methyl-1(S)-vinylpentyl)carbamate in 30 ml of methanol is admixed with 7.81 g of magnesium monoperoxyphthalate and stirred over 72 hours. The reaction mixture is poured onto water and extracted with tert-butyl methyl ether (2×). The combined organic phases are washed with water and brine, dried over sodium sulphate and concentrated by evaporation. The title compound is obtained from the residue by means of flash chromatography (SiO2 60F) as a yellowish oil. Rf=0.30 (1:1 EtOAc-heptane, run 2×); Rt=18.64 (gradient II).

c) tert-Butyl (3(S)-{[2-(3-methoxypropoxy)benzoylamino]methyl}-4-methyl-1(S)-vinylpentyl)carbamate The mixture of 2.38 g of potassium bis(trimethylsilyl)amide in 50 ml of diethyl ether is cooled to 0° C., admixed with 4.04 g of methyltriphenylphosphonium bromide and stirred over 30 minutes. The solution of 1.70 g of tert-butyl (1(S)-formyl-3(S)-{[2-(3-methoxypropoxy)-benzoylamino]methyl}4-methylpentyl)carbamate in 20 ml of diethyl ether is added dropwise. The reaction mixture is stirred at room temperature over 1 hour and subsequently poured onto 1M ammonium chloride solution and extracted with tert-butyl methyl ether (2×). The combined organic phases are washed with water and brine, dried over sodium sulphate and concentrated by evaporation. The title compound is obtained from the residue by means of flash chromatography (SiO2 60F) as a slightly yellowish oil. Rf=0.36 (1:1 EtOAc-heptane); Rt=5.05 (gradient I).

d) tert-Butyl (1(S)-formyl-3(S)-{[2-(3-methoxypropoxy)benzoylamino]methyl}-4-methylpentyl)carbamate The solution of 2.65 g of tert-butyl (1(S)-hydroxymethyl-3(S)-{[2-(3-methoxypropoxy)-benzoylamino]methyl}-4-methylpentyl)carbamate, 2.44 ml of triethylamine in 20 ml of dichloromethane is cooled to 0° C. The solution of 3.07 g of sulphur trioxide-pyridine complex in 12 ml of dimethyl sulphoxide is added dropwise over 1 hour and then the mixture is stirred for another 1 hour. The reaction mixture is admixed with 20 ml of ice-water and extracted with dichloromethane (3×). The combined organic phases are washed with 10% aqueous sodium hydrogensulphate solution, water, 1M sodium hydrogencarbonate solution and brine, dried over sodium sulphate and concentrated by evaporation. The title compound is obtained as a slightly yellowish foam. Rf=0.33 (3:1 EtOAc-heptane); Rt=4.65 (gradient I).

e) tert-Butyl (1(S)-hydroxymethyl-3(S)-{[2-(3-methoxypropoxy)benzoylamino]methyl}-4-methylpentyl)carbamate The solution of 3.70 g of tert-butyl 4(S)-(2(S)-{[2-(3-methoxypropoxy)benzoylamino]methyl}-3-methylbutyl)-2,2-dimethyloxazolidine-3-carbamate in 70 ml of methanol is admixed with 0.143 g of p-toluenesulphonic acid monohydrate and stirred at room temperature over 14 hours. The reaction mixture is concentrated by evaporation and the title compound is obtained from the residue by means of flash chromatography (SiO2 60F) as a slightly yellowish oil. Rf=0.16 (3:1 EtOAc-heptane); Rt=4.23 (gradient I).

f) tert-Butyl 4(S)-(2(S)-{[2-(3-methoxypropoxy)benzoylamino]methyl}-3-methylbutyl)-2,2-dimethyloxazolidine-3-carbamate The solution of 2.99 g of 2-(3-methoxypropoxy)benzoic acid [179992-98-4] and 3.95 ml of triethylamine in 60 ml of dichloromethane is cooled to 15° C. and admixed with 3.70 g of bis-(2-oxo-3-oxazolidynyl)phosphinoyl chloride. The mixture is stirred over 1 hour and subsequently admixed with the solution of 2.22 g of tert-butyl 4(S)-(2(S)-aminomethyl-3-methylbutyl)-2,2-dimethyloxazolidine-3-carbamate in 3 ml of dichloromethane and 0.703 g of 4-dimethylaminopyridine, and stirred overnight. The reaction mixture is poured onto 1M NaOH and extracted with tert-butyl methyl ether (2×). The combined organic phases are washed with water and brine, dried over sodium sulphate and concentrated by evaporation. The title compound is obtained from the residue by means of flash chromatography (SiO2 60F) as a slightly yellowish oil. Rf=0.29 (1:1 EtOAc-heptane); Rt=5.49 (gradient I).

g) tert-Butyl 4(S)-(2(S)-aminomethyl-3-methylbutyl)-2,2-dimethyloxazolidine-3-carbamate The solution of 2.65 g of tert-butyl 4(S)-(2(S)-azidomethyl-3-methylbutyl)-2,2-dimethyl-oxazolidine-3-carboxylate in 130 ml of ethyl acetate is hydrogenated at room temperature in the presence of 0.665 g of 10% Pd/C over 1 hour. The reaction mixture is subsequently clarified by filtration and the filtrate is concentrated by evaporation. The title compound is obtained from the residue by means of flash chromatography (SiO2 60F) as a greyish oil. Rf=0.25 (200:20:1 dichloromethane-methanol-25% conc. ammonia).

h) tert-Butyl 4(S)-(2(S)-azidomethyl-3-methylbutyl)-2,2-dimethyloxazolidine-3-carboxylate The mixture of 3.47 g of tert-butyl 4(S)-(2(S)-methanesulphonyloxymethyl-3-methylbutyl)-2,2-dimethyloxazolidine-3-carboxyiate and 3.57 g of sodium azide in 50 ml of 1,3-dimethyl-3,4,5,6-tetrahydro-2(1H)-pyrimidinone is stirred at 50° C. over 3 hours. The reaction mixture is cooled, poured onto water and extracted with diethyl ether (3×). The combined organic phases are washed successively with water (2×) and brine, dried over sodium sulphate and concentrated by evaporation. The title compound is obtained from the residue by means of flash chromatography (SiO2 60F) as a slightly yellowish oil. Rf=0.63 (1:1 EtOAc-heptane); Rt=5.86 (gradient I).

i) tert-Butyl 4(S)-(2(S)-methanesulphonyloxymethyl-3-methylbutyl)-2,2-dimethyloxazolidine-3-carboxylate The solution of 2.84 g of tert-butyl 4(S)-(2(S)-hydroxymethyl-3-methylbutyl)-2,2-dimethyl-oxazolidine-3-carboxylate in 100 ml of dichloromethane is admixed at 0° C. successively with 1.41 ml of triethylamine and 0.76 ml of methanesulphonyl chloride. The reaction mixture is stirred at 0° C. over 1 hour and subsequently concentrated by evaporation. The title compound is obtained from the residue by means of flash chromatography (SiO2 60F) as a slightly yellowish oil. Rf=0.30 (1:2 EtOAc-heptane); Rt=5.03 (gradient I).

k) tert-Butyl 4(S)-(2(S)-hydroxymethyl-3-methylbutyl)-2,2-dimethyloxazolidine-3-carboxylate A solution of 3.58 g of tert-butyl 4(S)-(2(S)-benzyloxymethyl-3-methylbutyl)-2,2-dimethyl-oxazolidine-3-carboxylate in 100 ml of tetrahydrofuran is hydrogenated at room temperature in the presence of 0.720 g of 10% Pd/C over 1 hour. The reaction mixture is clarified by filtration and the filtrate is concentrated by evaporation. The title compound is obtained from the residue by means of flash chromatography (SiO2 60F) as a yellowish oil. Rf=0.28 (1:2 EtOAc-heptane); Rt=4.48 (gradient I).

l) tert-Butyl 4(S)-(2(S)-benzyloxymethyl-3-methyl-butyl)-2,2-dimethyloxazolidine-3-carboxylate The solution of 3.51 g of tert-butyl (3(S)-benzyloxymethyl-1(S)-hydroxymethyl-4-methyl-pentyl)carbamate in 20 ml of dichloromethane is cooled to 0° C. and admixed successively with 0.076 g of p-toluenesulphonic acid monohydrate and 2.6 ml of 2-methoxypropene. The reaction mixture is stirred at room temperature for another 16 hours and subsequently poured onto 1M sodium hydrogencarbonate solution, extracted with tert-butyl methyl ether (2×). The combined organic phases are washed with brine, dried over sodium sulphate and concentrated by evaporation. The title compound is obtained from the residue by means of flash chromatography (SiO2 60F) as a yellowish oil. Rf=0.42 (1:4 EtOAc-heptane); Rt=6.20 (gradient I).

m) tert-Butyl (3(S)-benzyloxymethyl-1(S)-hydroxymethyl-4-methylpentyl)carbamate The stirred solution of 5.0 g of methyl 4(S)-benzyloxymethyl-2(S)-tert-butoxycarbonylamino-5-methylhexanecarboxylate [CAS 180182-92-7] in 80 ml of tetrahydrofuran is admixed in portions with 0.660 g of lithium borohydride. The reaction mixture is stirred for another 3 hours, admixed cautiously with 25 ml of methanol and concentrated by evaporation at 40° C. The residue is dissolved once more in 70 ml of methanol and again concentrated by evaporation at 40° C. The residue is admixed with 1M HCl (cold) and extracted with dichloromethane (3×). The combined organic phases are washed with water, dried over sodium sulphate, filtered and concentrated by evaporation. The title compound is obtained from the residue by means of flash chromatography (SiO2 60F) as a colourless oil. Rf=0.32 (1:1 EtOAc-heptane); Rt=4.86 (gradient I).

According to the processes described in Example 1, the following compounds are prepared in an analogous manner:

EXAMPLES

6 N-(4(S)-amino-5(S)-hydroxy-2(S)-isopropyl-6-piperidin-1-ylhexyl)-2-(4-methoxy-butoxy)benzamide dihydrochloride
11 N-(4(S)-amino-5(S)-hydroxy-2(S)-isopropyl-6-morpholin-4-ylhexyl)-2-(4-methoxy-butoxy)benzamide dihydrochloride
12 N-[4(S)-amino-6-(9-azabicyclo[3.3.1]non-9-yl)-5(S)-hydroxy-2(S)-isopropylhexyl]-2-(4-methoxybutoxy)benzamide dihydrochloride
13 N-[4(S)-amino-6-(cis-2,6-dimethylpiperidin-1-yl)-5(S)-hydroxy-2(S)isopropylhexyl]-2-(4-methoxybutoxy)benzamide dihydrochloride
14 N-[4(S)-amino-6-(3-methylpiperidin-1-yl)-5(S)-hydroxy-2(S)-isopropylhexyl]-2-(4-methoxybutoxy)benzamide dihydrochloride
15 N-[4(S)-amino-6-(4-methylpiperidin-1-yl)-5(S)-hydroxy-2(S)-isopropylhexyl]-2-(4-methoxybutoxy)benzamide dihydrochloride
16 N-(4(S)-amino-6-sec-(S)-butylamino-5(S)-hydroxy-2(S)-isopropylhexyl)-2-(4-methoxy-butoxy)benzamide dihydrochloride
18 N-(4(S)-amino-6-tert-butylamino-5(S)-hydroxy-(S)-isopropylhexyl)-2-(4-methoxy-butoxy)benzamide dihydrochloride
19 N-(4(S)-amino-5(S)-hydroxy-2(S)-isopropyl-6-isopropylaminohexyl)-2-(4-methoxy-butoxy)benzamide dihydrochloride
20 N-(4(S)-amino-6-sec-(R)-butylamino-5(S)-hydroxy-2(S)-isopropylhexyl)-2-(4-methoxy-butoxy)benzamide dihydrochloride
21 N-[4(S)-amino-6-(cyclopropylmethylamino)-5(S)-hydroxy-2(S)-isopropylhexyl]-2-(4-methoxybutoxy)benzamide dihydrochloride
22 N-[4(S)-amino-6-(1,1-dimethylpropylamino)-5(S)-hydroxy-2(S)-isopropylhexyl]-2-(4-methoxybutoxy)benzamide dihydrochloride
23 N-(4(S)-amino-6-ethylamino-5(S)-hydroxy-2(S)-isopropylhexyl)-2-(4-methoxybutoxy)-benzamide dihydrochloride
24 N-(4(S)-amino-5(S)-hydroxy-2(S)-isopropyl-6-propylaminohexyl)-2-(4-methoxy-butoxy)benzamide dihydrochloride
25 N-[4(S)-amino-6-(1-ethylpropylamino)-5(S)-hydroxy-2(S)-isopropylhexyl]-2-(4-methoxybutoxy)benzamide dihydrochloride
26 N-(4(S)-amino-6-cyclopentylamino-5(S)-hydroxy-2(S)-isopropylhexyl)-2-(4-methoxy-butoxy)benzamide dihydrochloride
27 N-[4(S)-amino-5(S)-hydroxy-2(S)-isopropyl-6-(2(R)-methylpiperidin-1-yl)hexyl]-2-(4-methoxybutoxy)benzamide dihydrochloride
28 N-[4(S)-amino-5(S)-hydroxy-2(S)-isopropyl-6-(2(S)-methylpiperidin-1-yl)hexyl]-2-(4-methoxybutoxy)benzamide dihydrochloride
29 N-(4(S)-amino-5(S)-hydroxy-6-isobutylamino-2(S)-isopropylexyl)-2-(4-methoxy-butoxy)benzamide dihydrochloride
30 N-[4(S)-amino-6-(1-ethyl-1-methylpropylamino)-5(S)-hydroxy-2(S)-isopropylhexyl]-2-(4-methoxybutoxy)benzamide dihydrochloride
31 N-(4(S)-amino-6-cyclopropylamino-5(S)-hydroxy-2(S)-isopropylhexyl)-2-(4-methoxy-butoxy)benzamide dihydrochloride
32 N-(4(S)-amino-6-azepan-1-yl-5(S)-hydroxy-2(S)-isopropylhexyl)-2-(4-methoxybutoxy)-benzamide dihydrochloride
33 N-[4(S)-amino-5(S)-hydroxy-2(S)-isopropyl-6-(1(S)-methylpentylamino)hexyl]-2-(4-methoxybutoxy)benzamide dihydrochloride
34 N-[4(S)-amino-5(S)-hydroxy-2(S)-isopropyl-6-(1(R)-methylpentylamino)hexyl]-2-(4-methoxybutoxy)benzamide dihydrochloride
35 N-(4(S)-amino-5(S)-hydroxy-2(S)-isopropyl-6-pyrrolidin-1-ylhexyl)-2-(4-methoxy-butoxy)benzamide dihydrochloride
36 N-(4(S)-amino-6-benzylamino-5(S)-hydroxy-2(S)-isopropylhexyl)-2-(4-methoxy-butoxy)benzamide dihydrochloride
66 N-[4(S)-amino-5(S)-hydroxy-2(S)-isopropyl-6-(2(R)-methoxymethylpyrrolidin-1-yl)-hexyl]-2-(4-methoxybutoxy)benzamide hydrochloride
71 N-[4(S)-amino-6-(1-carbamoylethylamino)-5(S)-hydroxy-2(S)-isopropylhexyl]-2-(4-methoxybutoxy)benzamide dihydrochloride
72 N-[6-(3(S)-acetylaminopyrrolidin-1-yl)-4(S)-amino-5(S)-hydroxy-2(S)-isopropylhexyl]-2-(4-methoxybutoxy)benzamide hydrochloride

EXAMPLE 2

N-[4(S)-Amino-6-(2,2-dimethylpropionylamino)-5(S)-hydroxy-2(S)-isopropylhexyl]-2-(3-methoxypropoxy)benzamide hydrochloride

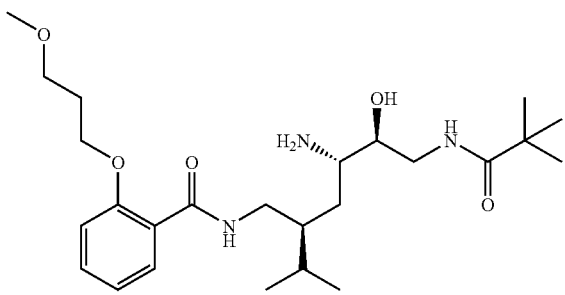

The solution of 0.030 g of tert-butyl (1(S)-[2-(2,2-dimethylpropionylamino)-1(S)-hydroxyethyl]-3(S)-{[2-(3-methoxypropoxy)benzoylamino]methyl}-4-methylpentyl)carbamate in 1 ml of 4M HCl (in dioxane) is stirred at 0° C. to 20° C. over 2 hours, subsequently concentrated by evaporation to dryness—the residue is dissolved in 1 ml of tert-butanol, frozen and lyophilized under high vacuum. The title compound is obtained as a white powder. Rf=0.20 (200:20:1 dichloromethane-methanol-25% conc. ammonia); Rt=3.55 (gradient I).

The starting materials are prepared as follows:

a) tert-Butyl (1(S)-[2-(2,2-dimethylpropionylamino)-1(S)-hydroxyethyl]-3(S)-{[2-(3-methoxy-propoxy)benzoylamino]methyl}-4-methylpentyl)carbamate The stirred solution of 0.030 g of tert-butyl (1(S)-(2-amino-1(S)-hydroxyethyl)-3(S)-{[2-(3-methoxypropoxy)benzoylamino]methyl}4-methylpentyl)carbamate in 0.60 ml of ethyl acetate is admixed successively with 0.60 ml of 2M sodium carbonate solution and 0.012 ml of pivaloyl chloride and stirred at room temperature over 1 hour. The reaction solution is admixed with water and extracted with ethyl acetate (2×). The combined organic phases are washed with water and brine, dried over sodium sulphate and concentrated by evaporation. The title compound is obtained from the residue by means of flash chromatography (SiO2 60F) as a colourless oil. Rf=0.45 (200:20:1 dichloromethane-methanol-25% conc. ammonia); Rt=4.71 (gradient I)

b) tert-Butyl (1(S)-(2-amino-1(S)-hydroxyethyl)-3(S)-{[2-(3-methoxypropoxy)benzoylamino]-methyl}-4-methylpentyl)carbamate The solution of 0.520 g of tert-butyl (1(S)-2-azido-1(S)-hydroxyethyl)-3(S)-{[2-(3-methoxy-propoxy)benzoylamino]methyl}-4-methylpentyl)carbamate in 15 ml of methanol is hydrogenated in the presence of 0.106 g of 10% Pd/C over 1 hour. The reaction mixture is clarified by filtration and concentrated by evaporation. The title compound is obtained from the residue by means of flash chromatography (SiO2 60F) as a slightly greyish oil. Rf=0.10 (200:20:1 dichloromethane-methanol-25% ammonia); Rt=14.42 (gradient II).

c) tert-Butyl (1(S)-(2-azido-1(S)-hydroxyethyl)-3(S)-{[2-(3-methoxypropoxy)benzoylamino]-methyl}4-methylpentyl)carbamate The solution of 0.600 g of tert-butyl (3(S)-{[2-(3-methoxypropoxy)benzoylamino]methyl}-4-methyl-1(S)—(R)-oxiranylpentyl)carbamate (Example 1b) in 12 ml of methanol is admixed with 0.208 g of sodium azide and 0.123 g of ammonium chloride, and stirred at reflux over 6 hours. The reaction solution is cooled, poured onto ice-water and extracted with tert-butyl methyl ether (2×). The combined organic phases are washed with water and brine, dried over sodium sulphate and concentrated by evaporation. The title compound is obtained from the residue by means of flash chromatography (SiO2 60F) as a colourless oil. Rf=0.37 (2:1 EtOAc-heptane); Rt=18.95 (gradient II).

EXAMPLE 3

N-{4(S)-Amino-5(S)-hydroxy-2(S)-isopropyl-6-[2-methyl-2-(tetrahydropyran-4-yl)propionyl-amino]hexyl}-2-(3-methoxypropoxy)benzamide hydrochloride

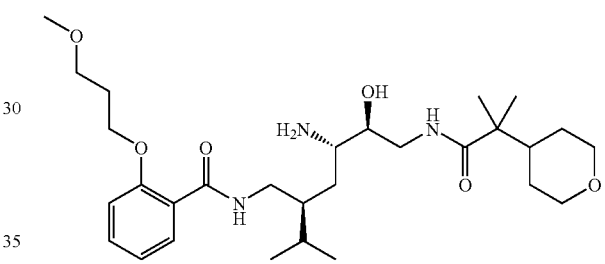

The solution of 0.030 g of tert-butyl (1(S)-{1(S)-hydroxy-2-[2-methyl-2-(tetrahydropyran-4-yl)-propionylamino]ethyl}-3(S)-{[2-(3-methoxypropoxy)benzoylamino]methyl}-4-methylpentyl)-carbamate in 1 ml of 4M HCl (in dioxane) is stirred at 0° C. to 20° C. over 2 hours and subsequently concentrated by evaporation to dryness, and the residue is dissolved in 1 ml of tert-butanol, frozen and lyophilized under high vacuum. The title compound is obtained as a white powder. Rf=0.23 (200:20:1 dichloromethane-methanol-25% conc. ammonia); Rt=3.46 (gradient I).

The starting material is prepared as follows:

a) tert-Butyl (1(S)-{1(S)-hydroxy-2-[2-methyl-2-(tetrahydropyran-4-yl)propionylamino]ethyl}-3(S)-{[2-(3-methoxypropoxy)benzoylamino]methyl}-4-methylpentyl)carbamate A solution of 0.017 g of 2-methyl-2-(tetrahydropyran-4-yl)propionic acid in 1 ml of dichloromethane is admixed at 0° C. with 0.021 ml of 1-chloro-N,N-trimethylpropenylamine and the reaction solution is stirred at 0° over 1 hour. The reaction solution is concentrated by evaporation and the residue is dissolved in 0.6 ml of ethyl acetate. The solution is added to a mixture of 0.030 g of tert-butyl (1(S)-(2-amino-1(S)-hydroxyethyl)-3(S)-{[2-(3-methoxypropoxy)benzoylamino]methyl}-4-methylpentyl)carbamate (Example 2b) in 0.5 ml of ethyl acetate and 0.6 ml of saturated aqueous sodium carbonate solution, and the reaction mixture is stirred at room temperature over 1.5 hours. The reaction solution is admixed with water and extracted with ethyl acetate (2×). The combined organic phases are washed with water and brine, dried over sodium sulphate and concentrated by evaporation. The title compound is obtained from the residue by means of flash chromatography (SiO2 60F) as a yellowish oil. Rf=0.52 (200: 20:1 dichloromethane-methanol-conc. ammonia); Rt=4.56 (gradient I)

According to the processes described in Examples 1-3, the following compounds are prepared in an analogous manner:

EXAMPLES

7 N-[4(S)-amino-6-(2,2-dimethylpropionylamino)-5(S)-hydroxy-2(S)-isopropyhexyl]-2-(4-methoxybutoxy)benzamide hydrochloride 8 N-{4(S)-amino-5(S)-hydroxy-2(S)-isopropyl-6-[2-methyl-2-(tetrahydropyran-4-yl)-propionylamino]hexyl}-2-(4-methoxybutoxy)benzamide hydrochloride 39 N-[4(S)-amino-6-(2-cyclohexyl-2-methylpropionylamino)-5(S)-hydroxy-2(S)-isopropyl-hexyl]-2-(4-methoxybutoxy)benzamide hydrochloride 40 N-{4(S)-amino-5(S)-hydroxy-2(S)-isopropyl-6-[(1-phenylcyclobutanecarbonyl)amino]-hexyl}-2-(4-methoxybutoxy)benzamide hydrochloride 41 N-[4(S)-amino-6-(2,2-dimethylhexanoylamino)-5(S)-hydroxy-2(S)-isopropylhexyl]-2-(4-methoxybutoxy)benzamide hydrochloride 42 N-(4(S)-amino-6-{[1-(4-chlorophenyl)cyclobutanecarbonyl]amino}-5(S)-hydroxy-2(S)-isopropylhexyl)-2-(4-methoxybutoxy)benzamide hydrochloride 43 N-[4(S)-amino-5(S)-hydroxy-2(S)-isopropyl-6-(2-methyl-2-m-tolylpropionylamino)-hexyl]-2-(4-methoxybutoxy)benzamide hydrochloride 44 N-[4(S)-amino-6-(2-cyclopentyl-2-methylpropionylamino)-5(S)-hydroxy-2(S)-isopropyl-hexyl]-2-(4-methoxybutoxy)benzamide hydrochloride 45 N-[4(S)-amino-5(S)-hydroxy-2(S)-isopropyl-6-(2-methyl-2-morpholin-4-ylpropionyl-amino)hexyl]-2-(4-methoxybutoxy)benzamide dihydrochloride 46 N-{4(S)-amino-6-[2-(3-fluorophenyl)-2-methylpropionylamino]-5(S)-hydroxy-2(S)-isopropylhexyl}-2-(4-methoxybutoxy)benzamide hydrochloride 47 N-{4(S)-amino-6-[(1-cyclohexylcyclobutanecarbonyl)amino]-5(S)-hydroxy-2(S)-isopropylhexyl}2-(4-methoxybutoxy)benzamide hydrochloride 48 N-[4(S)-amino-5(S)-hydroxy-2(S)-isopropyl-6-(2-methyl-2-pyridin-3-ylpropionylamino)-hexyl]-2-(4-methoxybutoxy)benzamide dihydrochloride 49 N-[4(S)-amino-6-(3-chloro-2,2-dimethylpropionylamino)-5(S)-hydroxy-2(S)-isopropyl-hexyl]-2-(4-methoxybutoxy)benzamide hydrochloride 50 N-[6-(2-acetylamino-2-methylpropionylamino)-4(S)-amino-5(S)-hydroxy-2(S)-isopropylhexyl]-2-(4-methoxybutoxy)benzamide hydrochloride 51 N-{4(S)-amino-5(S)-hydroxy-2(S)-isopropyl-6-[(1-trifluoromethylcyclobutanecarbonyl)-amino]hexyl}-2-(4-methoxybutoxy)benzamide hydrochloride 52 N-[4(S)-amino-6-(2-cyclohexyloxy-2-methylpropionylamino)-5(S)-hydroxy-2(S)-isopropylhexyl]-2-(4-methoxybutoxy)benzamide hydrochloride 53 N-[4(S)-amino-5(S)-hydroxy-2(S)-isopropyl-6-(2-methoxy-2-methylpropionylamino)-hexyl]-2-(4-methoxybutoxy)benzamide hydrochloride 54 N-[4(S)-amino-5(S)-hydroxy-2(S)-isopropyl-6-(2-methyl-2-piperidin-1-ylpropionyl-amino)hexyl]-2-(4-methoxybutoxy)benzamide dihydrochloride 55 N-{4-amino-5-hydroxy-2-isopropyl-6-[(1-methylcyclohexanecarbonyl)amino]hexyl}-2-(4-methoxybutoxy)benzamide hydrochloride 56 N-{4(S)-amino-5(S)-hydroxy-6-[2-(1H-indol-3-yl)-2-methylpropionylamino]-2(S)-isopropylhexyl}-2-(4-methoxybutoxy)benzamide hydrochloride 57 N-[4(S)-amino-5(S)-hydroxy-2(S)-isopropyl-6-(2-methoxypropionylamino)hexyl]-2-(4-methoxybutoxy)benzamide hydrochloride 58 N-(3(S)-amino-2(S)-hydroxy-5(S)-{[2-(4-methoxybutoxy)benzoylamino]methyl}-6-methylheptyl)adamantane-1-carboxamide hydrochloride 59 N-{4(S)-amino-6-[(2,2-dimethylpropionyl)hydroxyamino]-5(S)-hydroxy-2(S)-isopropyl-hexyl}-2-(4-methoxybutoxy)benzamide hydrochloride 63 N-[4(S)-amino-6-(3,3-dimethylureido)-5(S)-hydroxy-2(S)-isopropylhexyl]-2-(4-methoxybutoxy)benzamide hydrochloride 64 N-(4(S)-amino-6-benzoylamino-5(S)-hydroxy-2(S)-isopropylhexyl)-2-(4-methoxy-butoxy)benzamide hydrochloride 67 N-[4(S)-amino-6-(formylisopropylamino)-5(S)-hydroxy-2(S)-isopropylhexyl]-2-(4-methoxybutoxy)benzamide hydrochloride 70 N-[6-(acetylmethylamino)-4(S)-amino-5(S)-hydroxy-2(S)-isopropylhexyl]-2-(4-methoxybutoxy)benzamide hydrochloride 73 N-[4(S)-amino-5(S)-hydroxy-2(S)-isopropyl-6-(2-methyl-2-pyridin-2-ylpropionylamino)-hexyl]-2-(4-methoxybutoxy)benzamide dihydrochloride 74 N-[4(S)-amino-5(S)-hydroxy-2(S)-isopropyl-6-(2-methyl-2-piperidin-4-ylpropionyl-amino)hexyl]-2-(4-methoxybutoxy)benzamide dihydrochloride The starting materials are prepared as follows:

a) tert-Butyl 4-(1-methoxycarbonyl-1-methylethyl) piperidin-1-carboxylate 0.052 g of methyl 2-methyl-2-piperidin-4-ylpropionate hydrochloride are taken up in 2 ml of dioxane and the mixture is admixed with 2 ml of 3M NaOH. The reaction mixture is stirred at room temperature for 30 minutes and 0.079 g of di-tert-butyl dicarbonate are added. The reaction mixture is subsequently stirred at room temperature for 16 hours, adjusted to pH=6 with 2M HCl and extracted with ethyl acetate (2×). The combined organic phases are washed with brine, dried over sodium sulphate and concentrated. The title compound is obtained from the residue by means of flash chromatography (SiO2 60F) as a colourless oil. Rf=0.45 (1:2 EtOAc-heptane).

b) Methyl 2-methyl-2-piperidin-4-ylpropionate hydrochloride 0.115 g of methyl 2-methyl-2-pyridin-4-ylpropionate (CAS 79757-27-0) are dissolved in 5 ml of methanol in an autoclave. The solution is admixed with 0.35 ml of 1.2M HCl in methanol and 0.012 g of platinum (IV) oxide, and the reaction mixture is hydrogenated at 4 bar and 23° over 46 hours. The catalyst is filtered off through Hyflo and the filtrate is concentrated by evaporation. The title compound is obtained as a light brown solid. Rf 0.05 (200:20:1 dichloromethane-methanol-25% conc. ammonia).

75 N-[4(S)-amino-5(S)-hydroxy-2(S)-isopropyl-6-(3,3,3-trifluoro-2(R)-methoxy-2-phenyl-propionylamino) hexyl]-2-(4-methoxybutoxy)benzamide hydrochloride 76   N-[6-(N-acetylhydrazino)-4(S)-amino-5(S)-hydroxy-2 (S)-isopropylhexyl]-2-(4-methoxy-butoxy)benzamide dihydrochloride
77   N-[4(S)-amino-5(S)-hydroxy-2(S)-isopropyl-6-(2(R)-methoxy-3-phenylpropionyl-amino)hexyl]-2-(4-methoxybutoxy)benzamide hydrochloride
78   N-[4(S)-amino-6-(3-cyclohexyl-2(R)-methoxypropionylamino)-5(S)-hydroxy-2(S)-isopropylhexyl]-2-(4-methoxybutoxy)benzamide hydrochloride
79   N-[4(S)-amino-5(S)-hydroxy-2(S)-isopropyl-6-(2-methyl-2-piperidin-3(R)-ylpropionyl-amino)hexyl]-2-(4-methoxybutoxy)benzamide dihydrochloride
80   N-[4(S)-amino-5(S)-hydroxy-2(S)-isopropyl-6-(2-methyl-2-piperidin-3(S)-ylpropionyl-amino)hexyl]-2-(4-methoxybutoxy)benzamide dihydrochloride
81   N-{4(S)-amino-5(S)-hydroxy-6-[2-(1H-imidazol-4-yl)-2-methylpropionylamino]-2(S)-isopropylhexyl}-2-(4-methoxybutoxy)benzamide hydrochloride
82   N-[4(S)-amino-6-(2,2-dimethyl-4-methylaminobutyrylamino)-5(S)-hydroxy-2(S)-isopropylhexyl]-2-(4-methoxybutoxy)benzamide dihydrochloride
83   N-{4(S)-amino-5(S)-hydroxy-6-[(2(S)-hydroxy-(S)-cyclopentanecarbonyl)amino]-2(S)-isopropylhexyl}-2-(4-methoxybutoxy)benzamide hydrochloride
84   N-[4(S)-amino-5(S)-hydroxy-2(S)-isopropyl-6-(2-methyl-2-piperidin-2(S)-ylpropionyl-amino)hexyl]-2-(4-methoxybutoxy)benzamide dihydrochloride
85   N-[4(S)-amino-5(S)-hydroxy-2(S)-isopropyl-6-(2-methyl-2-piperidin-2(R)-ylpropionyl-amino)hexyl]-2-(4-methoxybutoxy)benzamide dihydrochloride
86   N-[4(S)-amino-5(S)-hydroxy-2(S)-isopropyl-6-(2-methyl-2-(1,2-dihydrospiro[3H-indole-3,4'-piperidin]-1'-yl)propionylamino)hexyl]-2-(4-methoxybutoxy)benzamide dihydrochloride

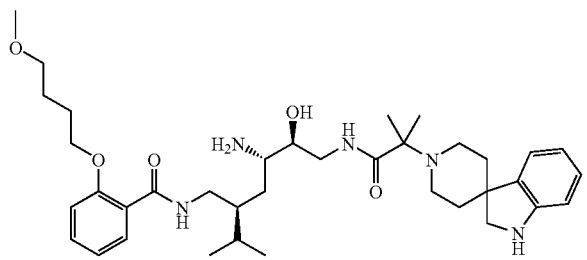

87 N-{4(S)-amino-5(S)-hydroxy-6-[2-(cis-4-hydroxycyclohex-1-yl)-2-methylpropionyl-amino]-2(S)-isopropylhexyl}-2-(4-methoxybutoxy)benzamide hydrochloride The starting materials are prepared as follows:

a) 2-(cis-4-Hydroxy-cyclohexyl)-2-methyl-propionic acid 0.200 g of 2-(cis-4-hydroxy-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is then neutralised with 1M HCl and concentrated by evaporation. The title compound is identified from the residue by means of flash chromatography (SiO2 60F) based on its Rf value.

b) 2-(cis-4-Hydroxy-cyclohexyl)-2-methyl-propionic acid methyl ester and 2-(trans-4-Hydroxy-cyclohexyl)-2-methyl-propionic acid methyl ester A solution of 2.0 g of 2-(cis/trans-4-hydroxy-cyclohexyl)-2-methyl-propionic acid in 40 ml of methanol is cooled to 0° C. 20 ml of a 2M trimethysilyldiazomethane solution in hexanes are added dropwise and the reaction solution is left to stand at room temperature for 1 hour. The solution is concentrated under reduced pressure and the residue taken up in ethyl acetate. The solution is washed with saturated aqueous sodium carbonate solution and brine, dried over sodium sulphate and concentrated by evaporation. The residue is purified by flash chromatography (SiO2 60F) to provide the title compounds as colourless oils, the cis isomer eluting first. Rf (cis)=0.11 (1:3 EtOAc-heptane); Rf (trans)=0.09 (1:3 EtOAc-heptane).

c) 2-(cis/trans-4-Hydroxy-cyclohexyl)-2-methyl-propionic acid 2.690 g of 2-(4-hydroxy-phenyl)-2-methyl-propionic acid (29913-51-7) are dissolved in 20 ml of water and 30 ml of 1M NaOH solution. 0.200 g of Raney-Nickel are added and the reaction mixture is hydrogenated at 50 bar and 150° C. for 24 hours. The catalyst is removed by filtration over Hyflo and the filtrate is concentrated by evaporation. The residue is taken up in 200 ml of water and the solution neutralized with 1M HCl to pH 6. The reaction mixture is then extracted with dichloromethane (2×200 ml) and ethyl acetate (2×20 ml) and the combined organic phases are dried over sodium sulphate and concentrated by evaporation to provide the title compounds as a ca. 1:4 mixture of cis/trans-isomers. The white solid is used for the next step without further purification.

88   N-{4(S)-amino-5(S)-hydroxy-6-[2-(trans-4-hydroxycyclohex-1-yl)-2-methylpropionyl-amino]-2(S)-isopropylhexyl}-2-(4-methoxybutoxy)benzamide hydrochloride
89   N-{4(S)-amino-5(S)-hydroxy-2(S)-isopropyl-6-[2-(cis-4-methoxycyclohex-1-yl)-2-methylpropionylamino]hexyl}-2-(4-methoxybutoxy)benzamide hydrochloride The starting materials are prepared as follows:

a) 2-(cis-4-Methoxy-cyclohexyl)-2-methyl-propionic acid 0.200 g of 2-(cis-4-methoxy-cyclohexyl)-2-methyl-propionic acid methyl ester are dissolved in 4 ml of methanol. 4 ml of a 1M aqueous lithium hydroxide solution is added and the mixture is stirred for 16 hours at room temperature. The reaction mixture is then neutralised with 1M HCl and concentrated under reduced pressure The title compound is identified from the residue by means of flash chromatography (SiO2 60F) based on its Rf value.

b) 2-(cis-4-Methoxy-cyclohexyl)-2-methyl-propionic acid methyl ester 0.500 g of 2-(cis-4-hydroxy-cyclohexyl)-2-methyl-propionic acid methyl ester (Example 87b) are dissolved in 5 ml of dry tetrahydrofuran. 0.120 g of sodium hydride (60% dispersion) is added in portions and the mixture stirred at 40° C. for 1 hour. Methyl iodide (0.233 ml) is added and the mixture heated to 40° C. for 5 hours. The reaction mixture is then cooled to room temperature, quenched with 5 ml of water and extracted with tert-butyl methyl ether (2×50 ml). The combined organic phases are dried over sodium sulphate and concentrated by evaporation. The title compound is identified from the residue by means of flash chromatography (SiO2 60F) based on its Rf value.

90   N-{4(S)-amino-5(S)-hydroxy-2(S)-isopropyl-6-[2-(trans-4-methoxycyclohex-1-yl)-2-methylpropionylamino]hexyl}2-(4-methoxybutoxy)benzamide hydrochloride 91   N-[4(S)-amino-6-(2-cyclohexyl-2(R)-methoxyacetylamino)-5(S)-hydroxy-2(S)-isopropylhexyl]-2-(4-methoxybutoxy)benzamide hydrochloride The starting material is prepared as follows:

a) (R)-Cyclohexyl-methoxy-acetic acid

An autoclave is charged with a solution of 1.00 g of (R)-α-methoxy-phenyl acetic acid in 20 ml methanol. 0.100 g of Nishimura catalyst are added and the mixture is hydrogenated at 4 bar and 20° C. for 1 hour. The mixture is filtered over Hyflo and the filtrate concentrated by evaporation to provide the title compound as a colourless oil. The crude material is used without further purification. Rf=0.84 (150:54:10:1 dichloromethane-methanol-water-acetic acid)

92   N-[4(S)-amino-5(S)-hydroxy-2(S)-isopropyl-6-(2(R)-methoxy-2-phenylacetylamino)-hexyl]-2-(4-methoxybutoxy)benzamide hydrochloride 93   N-[4(S)-amino-5(S)-hydroxy-2(S)-isopropyl-6-(2(R)-methoxy-3,3-dimethylbutyryl-amino)hexyl]-2-(4-methoxybutoxy)benzamide hydrochloride 94   N-[4(S)-amino-5(S)-hydroxy-2(S)-isopropyl-6-(3,3,3-trifluoro-2-methoxy-2-trifluoromethylpropionylamino)hexyl]-2-(4-methoxybutoxy)benzamide hydrochloride 95   N-[4(S)-amino-5(S)-hydroxy-2(S)-isopropyl-6-(3,3,3-trifluoro-2(R)-methoxy-2-methyl-propionylamino)hexyl]-2-(4-methoxybutoxy)benzamide hydrochloride 96   N-[4(S)-amino-5(S)-hydroxy-2(S)-isopropyl-6-(3,3,3-trifluoro-2(S)-methoxy-2-methyl-propionylamino)hexyl]-2-(4-methoxybutoxy)benzamide hydrochloride 97   N-[4(S)-amino-6-(2-cyclohexyl-3,3,3-trifluoro-2(R)-methoxypropionylamino)-5(S)-hydroxy-2(S)-isopropylhexyl]-2-(4-methoxybutoxy)benzamide hydrochloride 98   N-[4(S)-amino-5(S)-hydroxy-2(S)-isopropyl-6-(2(R)-methoxy-2-phenylpropionyl-amino)hexyl]-2-(4-methoxybutoxy)benzamide hydrochloride 99 N-[4(S)-amino-6-(2-cyclohexyl-2(R)-methoxypropionylamino)-5(S)-hydroxy-2(S)-isopropylhexyl]-2-(4-methoxybutoxy)benzamide hydrochloride 100   N-{4(S)-amino-5(S)-hydroxy-2(S)-isopropyl-6-[(1-methoxycyclopentanecarbonyl)-amino]hexyl}-2-(4-methoxybutoxy)benzamide hydrochloride 101   N-{4(S)-amino-5(S)-hydroxy-2(S)-isopropyl-6-[(1-methoxycyclohexanecarbonyl)-amino]hexyl}-2-(4-methoxybutoxy)benzamide hydrochloride 102 N-[4(S)-Amino-5(S)-hydroxy-2(S)-isopropyl-6-(2-methyl-2-piperidin-3(R,S)-yl-propionylamino)-hexyl]-2-(4-methoxy-butoxy)-benzamide dihydrochloride The starting materials are prepared according to the processes described in Example 74.

103   N-{4(S)-Amino-5(S)-hydroxy-2(S)-isopropyl-6-[2-methyl-2-(1-methyl-piperidin-3(R,S)-yl)-propionylamino]-hexyl}2-(4-methoxy-butoxy)-benzamide dihydrochloride The starting materials are prepared as follows:

a) 2-Methyl-2-(1-methyl-piperidin-3(R,S)-yl)-propionic acid 0.200 g of 2-methyl-2-(1-methyl-piperidin-3(R,S)-yl)-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml). The organic phases are combined and concentrated by evaporation. The residue is purified by means of flash chromatography (SiO2 60F) to provide the title compound as a colourless oil. Rf 0.15 (150:54:10:1 dichloromethane-methanol-acetic acid-water).

b) 2-Methyl-2-(1-methyl-piperidin-3(R,S)-yl)-propionic acid methyl ester 0.370 g of 2-methyl-2-piperidin-3(R,S)-yl-propionic acid methyl ester hydrochloride (Example 102) are dissolved in 0.5 ml of 3M NaOH. 2 ml of formic acid and 0.19 ml of formaldehyde (35% aqueous solution) are added and the reaction solution is warmed to 60° C. for 20 hours. The solution is cooled to room temperature, neutralised with 3M NaOH to pH 8-9 and extracted with dichloromethane (3×10 ml). The combined organic phases are washed with water (10 ml), dried over sodium sulphate and concentrated by evaporation. The residue is purified by means of flash chromatography (SiO2 60F) to provide the title compound as a colourless oil. Rf 0.19 (200:20:1 dichlormethane-methanol-25% conc. ammonia).

104 N-[4(S)-Amino-5(S)-hydroxy-2(S)-isopropyl-6-(2-methyl-2-piperidin-2(R,S)-yl-propionylamino)-hexyl]-2-(4-methoxy-butoxy)-benzamide dihydrochloride 105 N-{4(S)-Amino-5(S)-hydroxy-2(S)-isopropyl-6-[2-methyl-2-(1-methyl-piperidin-2(R,S)-yl)-propionylamino]-hexyl}-2-(4-methoxy-butoxy)-benzamide dihydrochloride The starting materials are prepared according to the processes described in Example 103.

106   N-{4(S)-Amino-5(S)-hydroxy-6-[2(R,S)-(trans-2-hydroxy-cyclohexyl)-2-methyl-propionylamino]-2(S)-isopropyl-hexyl}2-(4-methoxy-butoxy)-benzamide hydrochloride The starting material is prepared as follows:

a) trans-2-[2-tert-Butyl-dimethyl-silanyloxy)-cyclohexyl]-2-methyl-propionic acid Imidazole (0.310 g) is added to a solution of 0.337 g trans-(2-(2-hydroxy-cyclohexyl)-2-methyl propionic acid (34440-72-7) and 0.682 g tert-butyl-dimethyl-chlorosilane in 7 ml of dry N,N-dimethylformamide. The mixture is left to stand at room temperature for 2 hours and is then warmed to 50° for 12 hours. The reaction mixture is poured onto water (30 ml) and the mixture is extracted with tert-butyl methyl ether (2×50 ml). The combined organic phases are washed with saturated aqueous sodium bicarbonate solution (30 ml) and brine (30 ml), dried over sodium sulphate and concentrated under reduced pressure. The residue is taken up in 9 ml of methanol and 3 ml of tetrahydrofuran and the resulting mixture is treated for 1 hour at room temperature with a 10% aqueous potassium carbonate solution (3 ml). The reaction solution is concentrated under reduced pressure to half of the initial volume and the pH is adjusted to 5 with 1M HCl. The mixture is extracted with tert-butyl methyl ether (2×50 ml) and the combined organic phases are washed with brine, dried over sodium sulphate and concentrated under reduced pressure. The residue is purified by means of flash chromatography (SiO2 60F) to provide the title compound as white solid. Rf 0.64 (1:2 EtOAc-heptane).

107 N-{4(S)-Amino-5(S)-hydroxy-6-[2-(3(S)-hydroxy-cyclohex-1(R)-yl)-2-methyl-propionylamino]-2(S)-isopropyl-hexyl}2-(4-methoxy-butoxy)-benzamide hydrochloride The starting materials are prepared as follows:

a) 2-(3(S)-Hydroxy-cyclohex-1(R)-yl)-2-methyl-propionic acid 1.00 g of 2-(cis-3-hydroxy-cyclohexyl)-2-methyl-propionic acid ethyl ester are dissolved in 30 ml of methanol. 30 ml of a 1M aqueous lithium hydroxide solution are added and the mixture is stirred for 16 hours at room temperature. The reaction mixture is neutralised with 1M HCl and concentrated by evaporation. The title compound is identified from the residue by means of flash chromatography (SiO2 60F) based on its Rf value.

b) 2-(3(S-Hydroxy-cyclohex-1(R)-yl)-2-methyl-propionic acid ethyl ester 3 ml of 1M tetrabutylammonium fluoride solution in tetrahydrofuran are added to a solution of 1.00 g of 2-[3(S)-(tert-butyl-dimethylsilanyloxy)-cyclohex-(1R)-yl]-2-methyl-propionic acid ethyl ester in 3 ml of tetrahydrofuran at 0° C. The reaction is left to stand at room temperature for 1 hour and is then diluted with tert-butyl methyl ether (20 ml) and washed with water (20 ml) and brine (20 ml). The organic layer is dried over sodium sulphate and concentrated by evaporation. The title compound is identified from the residue by means of flash chromatography (SiO2 60F) based on its Rf value.

c) 2-[3(S)-(tert-Butyl-dimethylsilanyloxy)-cyclohex-1(R)-yl]-2-methyl-propionic acid ethyl ester A solution of 21 ml lithium diisopropylamide (ca. 1M in tetrahydrofuran/hexanes) is cooled to −78° b. A solution of 3.72 g [3(S)-(tert-butyl-dimethyl-silanyl-oxy)-cyclohex-1(R)-yl]-acetic acid ethyl ester (197091-18-2) in 20 ml of tetrahydrofuran is added dropwise over a period of 15 minutes while maintaining the temperature at −78° C. The reaction solution is stirred for 30 minutes at −78° C. and methyl iodide (1.31 ml) is added in one portion. The reaction mixture is warmed to 0° C. over a period of 30 minutes and is then cooled again to −78° C. Lithium diisopropylamide-solution (21 ml) is added dropwise over a period of 15 minutes and the reaction mixture is stirred for 30 minutes at −78° C. 1.31 ml Methyl iodide are added in one portion and the reaction mixture is warmed to room temperature over a period of 16 hours. The reaction mixture is quenched with 0.1M HCl (50 ml) and is then extracted with tert-butyl methyl ether (3×50 ml). The combined organic phases are washed with brine (50 ml), dried over sodium sulphate and concentrated by evaporation. The title compound is identified from the residue by means of flash chromatography (SiO2 60F) based on its Rf value.

108 N-[4(S)-Amino-5(S)-hydroxy-6-(2-imidazol-1-yl-2-methyl-propionylamino)-2(S)-isopropyl-hexyl]-2-(4-methoxy-butoxy)-benzamide dihydrochloride The starting material is prepared as follows:

a) 2-Imidazol-1-yl-2-methyl-propionic acid 1.54 g of 2-imidazol-1-yl-2-methyl-propionic acid ethyl ester (73828-88-3) are dissolved in 20 ml of methanol. 20 ml of a 3M NaOH are added and the mixture is stirred for 16 hours at 60° C. The reaction mixture is then neutralised with 1M HCl and concentrated by evaporation. The title compound is identified from the residue by means of flash chromatography (SiO2 60F) based on its Rf value.

109 N-[4(S)-Amino-6-(2-cyano-2,2-dimethyl-acetylamino)-5(S)-hydroxy-2(S)-isopropyl-hexyl]-2-(4-methoxy-butoxy)-benzamide hydrochloride 110 N-{6-[trans-2-(4-Acetylamino-cyclohexyl)-2-methyl-propionylamino]-4(S)-amino-5(S)-hydroxy-2(S)-isopropyl-hexyl}-2-(4-methoxy-butoxy)-benzamide hydrochloride The starting materials are prepared as follows:

a) trans-2-(4-Acetylamino-cyclohexyl)-2-methyl-propionic acid 0.200 g of trans-2-(4-acetylamino-cyclohexyl)-2-methyl-propionic acid methyl ester are dissolved in 4 ml of methanol. 4 ml of a 1M aqueous lithium hydroxide solution are added and the mixture is stirred for 16 hours at room temperature. The reaction mixture is neutralised with 1M HCl and extracted with ethyl acetate (3×50 ml)—the combined organic phases are concentrated by evaporation. The title compound is identified from the residue by means of flash chromatography (SiO2 60F) based on its Rf value.

b) trans-2-(4-Acetylamino-cyclohexyl)-2-methyl-propionic acid methyl ester

A round bottom flask is charged with 0.422 g of trans-2-(4-azido-cyclohexyl)-2-methyl-propionic acid methyl ester. 0.71 ml of thiocetic acid are added and the solution is stirred for 1 hour at room temperature. After completion of the reaction, the reaction mixture is concentrated by evaporation. The title compound is identified from the residue by means of flash chromatography (SiO2 60F) based on its Rf value.

c) trans-2-(4-Azido-cyclohexyl)-2-methyl-propionic acid methyl ester

Sodium azide (0.761 g) is added to a solution of 0.898 g of cis-2-(4-methanesulfonyloxy-cyclohexl)-2-methyl-propionic acid methyl ester in 7 ml of N,N-dimethylformamide. The reaction mixture is warmed to 100° C. for 16 hours. The mixture is cooled to room temperature, diluted with 20 ml of water and extracted with tert-butyl methyl ether (3×30 ml). The combined organic phases are washed with brine (20 ml), dried over sodium sulphate and concentrated by evaporation. The title compound is identified from the residue by means of flash chromatography (SiO2 60F) based on its Rf value.

d) cis-2-(4-Methanesulfonyloxy-cyclohexl)-2-methyl-propionic acid methyl ester A solution of 1.00 g of 2-(cis-4-hydroxy-cyclohexyl)-2-methyl-propionic acid methyl ester (Example 87b), 1.38 ml triethylamine and 0.061 g of 4-dimethylaminopyridine in 20 ml of dichloromethane is cooled to 0° C. Methanesulfonylchloride (0.50 ml) is added and the solution is left to stand at room temperature for 16 hours. The solution is poured onto saturated aqueous sodium hydrogen carbonate solution and the phases are separated. The aqueous phase is extracted with dichloromethane (2×50 ml)—the combined organic phases are washed with brine (50 ml), dried over sodium sulphate and concentrated by evaporation. The title compound is identified from the residue by means of flash chromatography (SiO2 60F) based on its Rf value.

111 N-{6-[2-(3(S)-Acetylamino-cyclohex-1(R)-yl)-2-methyl-propionylamino]-4(S)-amino-5(S)-hydroxy-2(S)-isopropyl-hexyl}2-(4-methoxy-butoxy)-benzamide hydrochloride The starting materials are prepared according to the processes described in Example 110 starting from 2-(3(S)-hydroxy-cyclohex-1(R)-yl)-2-methyl-propionic acid ethyl ester (Example 107b).

112 N-[4(S)-Amino-6-(2,2-difluoro-2-phenyl-acetylamino)-5(S)-hydroxy-2(S)-isopropyl-hexyl]-2-(4-methoxy-butoxy)-benzamide hydrochloride 113 N-[4(S)-Amino-6-(2-cyclohexyl-2,2-difluoro-acetylamino)-5(S)-hydroxy-2(S)-isopropyl-hexyl]-2-(4-methoxy-butoxy)-benzamide hydrochloride 114 N-{4(S)-Amino-6-[2,2-difluoro-2-(tetrahydro-pyran-4-yl)-acetylamino]-5(S)-hydroxy-2(S)-isopropyl-hexyl}-2-(4-methoxy-butoxy)-benzamide hydrochloride

EXAMPLE 4

N-[4(S)-Amino-5(S)-hydroxy-2(S)-isopropyl-6-(2-oxopiperidin-1-yl)hexyl]-2-(3-methoxy-propoxy)benzamide hydrochloride

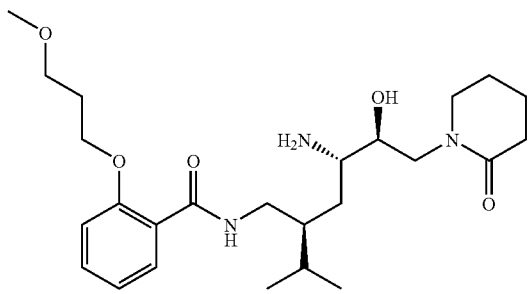

A solution of 0.051 g of 2-(3-methoxypropoxy)-N-{3-methyl-2(S)-[2-oxo-5(S)-(2-oxopiperidin-1-ylmethyl)oxazolidin-4(S)-ylmethyl]butyl}benzamide, 0.050 g of lithium hydroxide hydrate in 1.5 ml of ethanol and 1.5 ml of water is stirred at 100° C. over 2 hours. The reaction mixture is cooled to room temperature, poured onto ice-water and extracted with ethyl acetate (3×). The combined organic phases are dried over sodium sulphate and concentrated by evaporation. The title compound is obtained from the residue by means of flash chromatography (SiO2 60F) as the free base. This is dissolved in 0.5 ml of dioxane, admixed with 20 μl of 4N HCl/dioxane, frozen in liquid nitrogen and lyophilized under high vacuum overnight. The title compound is identified from the residue on the basis of the Rf value.

The starting material is prepared as follows:

a) 2-(3-Methoxypropoxy)-N-{3-methyl-2(S)-[2-oxo-5(S)-(2-oxopiperidin-1-ylmethyl)-oxazolidin-4(S)-ylmethyl]butyl}benzamide A mixture of 0.115 g of piperidin-2-one, 0.136 g of potassium tert-butoxide in 3 ml of dimethyl sulphoxide is stirred at room temperature over 30 minutes, admixed with 0.26 g of tert-butyl (3(S)-{[2-(3-methoxypropoxy)benzoylamino]methyl}-4-methyl-1(S)—(R)-oxiranylpentyl)-carbamate (Example 1b) and subsequently stirred further at room temperature overnight. The reaction mixture is poured onto ice-water and extracted with tert-butyl methyl ether (2×). The combined organic phases are washed successively with water and brine, dried over sodium sulphate and concentrated by evaporation. The title compound is identified from the residue by means of flash chromatography (SiO2 60F) on the basis of the Rf value.

According to the processes described in Example 4, the following compounds are prepared in an analogous manner:

EXAMPLES

9 N-[4(S)-amino-5(S)-hydroxy-2(S)-isopropyl-6-(2-oxopiperidin-1-yl)hexyl]-2-(4-methoxybutoxy)benzamide hydrochloride 17 N-[4(S)-amino-6-(3,3-dimethyl-2-oxopyrrolidin-1-yl)-5(S)-hydroxy-2(S)-isopropylhexyl]-2-(4-methoxybutoxy)benzamide hydrochloride 37 N-[4(S)-amino-5(S)-hydroxy-2(S)-isopropyl-6-(2-oxoazepan-1-yl)hexyl]-2-(4-methoxy-butoxy)benzamide hydrochloride 38 N-[4(S)-amino-6-(3,3-dimethyl-2-oxoazepan-1-yl)-5(S)-hydroxy-2(S)-isopropylhexyl]-2-(4-methoxybutoxy)benzamide hydrochloride 61 N-[4(S)-amino-5(S)-hydroxy-6-(4-hydroxy-2-oxopyrrolidin-1-yl)-2(S)-isopropylhexyl]-2-(4-methoxybutoxy)benzamide hydrochloride 62 N-[4(S)-amino-5(S)-hydroxy-2(S)-isopropyl-6-(2-oxotetrahydropyrimidin-1-yl)hexyl]-2-(4-methoxybutoxy)benzamide hydrochloride

EXAMPLE 5

N-[4(S)-Amino-5(S)-hydroxy-2(S)-isopropyl-6-(propane-2-sulphonylamino)hexyl]-2-(3-methoxypropoxy)benzamide hydrochloride

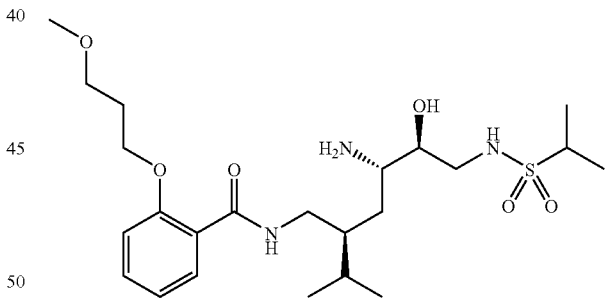

0.007 ml of propane-2-sulphonyl chloride is added at 0° C. to a solution of 0.0255 g of tert-butyl (1(S)-(2-amino-1(S)-hydroxyethyl)-3(S)-{[2-(3-methoxypropoxy)benzoylamino]methyl}-4-methylpentyl)carbamate (Example 2b) and 0.007 ml of triethylamine in 1 ml of dichloromethane. After 6 hours, the reaction mixture is concentrated by evaporation—the N-Boc intermediate is identified from the residue by means of flash chromatography (SiO2 60F) on the basis of the Rf value. This is dissolved in 0.82 ml of 4N HCl/dioxane—after 4 hours, the reaction mixture is concentrated by evaporation, and the residue is dissolved in 0.5 ml of tert-butanol, frozen in liquid nitrogen and lyophilized under high vacuum overnight. The title compound is identified from the residue on the basis of the Rf value.

According to the processes described in Example 5, the following compounds are prepared in an analogous manner:

EXAMPLES

10  N-[4(S)-amino-5(S)-hydroxy-2(S)-isopropyl-6-(propane-2-sulphonylamino)hexyl]-2-(4-methoxybutoxy)benzamide hydrochloride 60  N-(4(S)-amino-6-cyclopropanesulphonylamino-5(S)-hydroxy-2(S)-isopropylhexyl)-2-(4-methoxybutoxy)benzamide hydrochloride 65  N-(4(S)-amino-5(S)-hydroxy-2(S)-isopropyl-6-phenylmethanesulphonylaminohexyl)-2-(4-methoxybutoxy)benzamide hydrochloride 68  N-[4(S)-amino-5(S)-hydroxy-2(S)-isopropyl-6-(thiophene-2-sulphonylamino)hexyl]-2-(4-methoxybutoxy)benzamide hydrochloride 69  N-(4(S)-amino-6-benzenesulphonylamino-5(S)-hydroxy-2(S)-isopropylhexyl)-2-(4-methoxybutoxy)benzamide hydrochloride 115  N-[4(S)-Amino-5(S)-hydroxy-2(S)-isopropyl-6-(2-methyl-propane-2-sulfonylamino)-hexyl]-2-(4-methoxy-butoxy)-benzamide hydrochloride 116  N-[4(S)-Amino-6-(2-cyclohexyl-propane-2-sulfonylamino)-5(S)-hydroxy-2(S)-isopropyl-hexyl]-2-(4-methoxy-butoxy)-benzamide hydrochloride The starting materials are prepared as follows:

a) 2-Cyclohexyl-propane-2-sulfonyl chloride 2 mmol of phosphoroxytrichloride are added to a solution of 1 mmol of 2-cyclohexyl-propane-2-sulfonic acid in acetonitrile and the reaction mixture is heated to reflux for 2 hours. The reaction mixture is cooled to room temperature, carefully quenched by the addition of water and extracted with tert-butyl methyl ether. The organic phase is dried over sodium sulphate and concentrated by evaporation. The crude titel compound is used without further purification.

b) 2-Cyclohexyl-propane-2-sulfonic acid 10 ml of an aqueous hydrogen peroxide solution (30% wt) are added to a stirred solution of 1 mmol of 2-cyclohexyl-propane-2-thiol in acetic and the mixture is then heated at 60° C. overnight. The reaction mixture is cooled to room temperature and the solvent removed under reduced pressure. The crude titel compound is used without further purification.

c) 2-Cyclohexyl-propane-2-thiol 1 mmol of thiourea is added to a stirred solution of 1 mmol of (1-bromo-1-methyl-ethyl)-cyclohexane [BRN 2424910] in methanol and the mixture is stirred for 12 hours at room temperature. The solvent is removed under reduced pressure and the residue is then suspended in 10 ml of 2N NaOH and heated at 60° C. for 3 hours. The reaction mixture is cooled to room temperature and extracted with tert-butyl methyl ether (3×). The combined organic phases are dried over sodium sulphate and concentrated by evaporation. The crude titel compound is used without further purification.

The invention claimed is:

1. A compound selected from the group consisting of N-(4(S)-amino-5(S)-hydroxy-2(S)-isopropyl-6-piperidin-1-yl-hexyl)-2-(3-methoxypropoxy)benzamide dihydrochloride

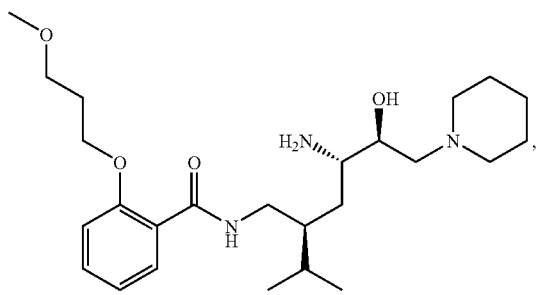

N-(4(S)-amino-5(S)-hydroxy-2(S)-isopropyl-6-piperidin-1-ylhexyl)-2-(4-methoxy-butoxy)benzamide dihydrochloride, N-(4(S)-amino-5(S)-hydroxy-2(S)-isopropyl-6-morpholin-4-ylhexyl)-2-(4-methoxy-butoxy)benzamide dihydrochloride, N-[4(S)-amino-6-(9-azabicyclo [3.3.1]non-9-yl)-5(S)-hydroxy-2(S)-isopropylhexyl]-2-(4-methoxybutoxy)benzamide dihydrochloride, N-[4(S)-amino-6-(cis-2,6-dimethylpiperidin-1-yl)-5(S)-hydroxy-2(S)-isopropylhexyl]-2-(4-methoxybutoxy)benzamide dihydrochloride, N-[4(S)-amino-6-(3-methylpiperidin-1-yl)-5(S)-hydroxy-2(S)-isopropylhexyl]-2-(4-methoxybutoxy)benzamide dihydrochloride, N-[4(S)-amino-6-(4-methylpiperidin-1-yl)-5(S)-hydroxy-2(S)-isopropylhexyl]-2-(4-methoxybutoxy)benzamide dihydrochloride, N-(4(S)-amino-6-sec-(S)-butylamino-5(S)-hydroxy-2(S)-isopropylhexyl)-2-(4-methoxy-butoxy)benzamide dihydrochloride, N-(4(S)-amino-6-tert-butylamino-5(S)-hydroxy-(S)-isopropylhexyl)-2-(4-methoxy-butoxy)benzamide dihydrochloride, N-(4(S)-amino-5(S)-hydroxy-2(S)-isopropyl-6-isopropylaminohexyl)-2-(4-methoxy-butoxy)benzamide dihydrochloride, N-(4(S)-amino-6-sec-(R)-butylamino-5(S)-hydroxy-2(S)-isopropylhexyl)-2-(4-methoxy-butoxy)benzamide dihydrochloride, N-[4(S)-amino-6-(cyclopropylmethylamino)-5(S)-hydroxy-2(S)-isopropylhexyl]-2-(4-methoxybutoxy)benzamide dihydrochloride, N-[4(S)-amino-6-(1,1-dimethylpropylamino)-5(S)-hydroxy-2(S)-isopropylhexyl]-2-(4-methoxybutoxy)benzamide dihydrochloride, N-(4(S)-amino-6-ethylamino-5(S)-hydroxy-2(S)-isopropylhexyl)-2-(4-methoxybutoxy)-benzamide dihydrochloride, N-(4(S)-amino-5(S)-hydroxy-2(S)-isopropyl-6-propylaminohexyl)-2-(4-methoxy-butoxy)benzamide dihydrochloride, N-[4(S)-amino-6-(1-ethylpropylamino)-5(S)-hydroxy-2(S)-isopropylhexyl]-2-(4-methoxy-butoxy)benzamide dihydrochloride, N-(4(S)-amino-6-cyclopentylamino-5(S)-hydroxy-2(S)-isopropylhexyl)-2-(4-methoxy-butoxy)benzamide dihydrochloride, N-[4(S)-amino-5(S)-hydroxy-2(S)-isopropyl-6-(2(R)-methylpiperidin-1-yl)hexyl]-2-(4-methoxybutoxy)benzamide dihydrochloride, N-[4(S)-amino-5(S)-hydroxy-2(S)-isopropyl-6-(2(S)-methylpiperidin-1-yl)hexyl]-2-(4-methoxybutoxy)benzamide dihydrochloride, N-(4(S)-amino-5(S)-hydroxy-6-isobutylamino-2(S)-isopropylhexyl)-2-(4-methoxy-butoxy)benzamide dihydrochloride, N-[4(S)-amino-6-(1-ethyl-1-methylpropylamino)-5(S)-hydroxy-2(S)-isopropylhexyl]-2-(4-methoxybutoxy)benzamide dihydrochloride, N-(4(S)-amino-6-cyclopropylamino-5(S)-hydroxy-2(S)-isopropylhexyl)-2-(4-methoxy-butoxy)benzamide dihydrochloride, N-(4(S)-amino-6-azepan-1-yl-5(S)-hydroxy-2(S)-isopropylhexyl)-2-(4-methoxybutoxy)-benzamide dihydrochloride, N-[4(S)-amino-5(S)-hydroxy-2(S)-isopropyl-6-(1(S)-methylpentylamino)hexyl]-2-(4-methoxybutoxy)benzamide dihydrochloride, N-[4(S)-amino-5(S)-hydroxy-2(S)-isopropyl-6-(1(R)-methylpentylamino)hexyl]-2-(4-methoxybutoxy)benzamide dihydrochloride, N-[4(S)-amino-5(S)-hydroxy-2(S)-isopropyl-6-pyrrolidin-1-ylhexyl)-2-(4-methoxy-butoxy)benzamide dihydrochloride, N-(4(S)-amino-6-benzylamino-5(S)-hydroxy-2(S)-isopropylhexyl)-2-(4-methoxy-butoxy)benzamide dihydrochloride, N-[4(S)-amino-5(S)-hydroxy-2(S)-isopropyl-6-(2(R)-methoxymethylpyrrolidin-1-yl)hexyl]-2-(4-methoxybutoxy)benzamide hydrochloride, N-[4(S)-amino-6-(1-carbamoylethylamino)-5(S)-hydroxy-2(S)-isopropylhexyl]-2-(4-methoxybutoxy)benzamide dihydrochloride, N-[6-(3(S)-acetylaminopyrrolidin-1-yl)-4(S)-amino-5(S)-hydroxy-2(S)-isopropylhexyl]-2-(4-methoxybutoxy)benzamide hydrochloride, N-[4(S)-Amino-6-(2,2-dimethylpropionylamino)-5(S)-hydroxy-2(S)-isopropylhexyl]-2-(3-methoxypropoxy)benzamide hydrochloride

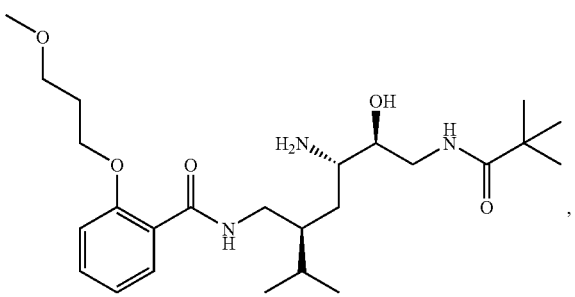

N-{4(S)-Amino-5(S)-hydroxy-2(S)-isopropyl-6-[2-methyl-2-(tetrahydropyran-4-yl)propionyl-amino]hexyl}-2-(3-methoxypropoxy)benzamide hydrochloride

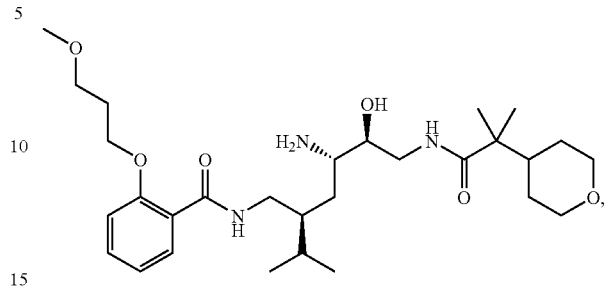

N-[4(S)amino-6-(2,2-dimethylpropionylamino)-5(S)-hydroxy-2(S)-isopropylhexyl]-2-(4-methoxybutoxy)benzamide hydrochloride, N-{4(S)-amino-5(S)-hydroxy-2(S)-isopropyl-6-[2-methyl-2-(tetrahydropyran-4-yl)-propionylamino]hexyl}-2-(4-methoxybutoxy)benzamide hydrochloride, N-[4(S)-amino-6-(2-cyclohexyl-2-methylpropionylamino)-5(S)-hydroxy-2(S)-isopropylhexyl]-2-(4-methoxybutoxy)benzamide hydrochloride, N-{4(S)-amino-5(S)-hydroxy-2(S)-isopropyl-6-[(1-phenylcyclobutanecarbonyl)amino]hexyl}-2-(4-methoxybutoxy)benzamide hydrochloride, N-[4(S)amino-6-(2,2-dimethylhexanoylamino)-5(S)-hydroxy-2(S)-isopropylhexyl]-2-(4-methoxybutoxy)benzamide hydrochloride, N-(4(S)-amino-6-{[1-(4-chlorophenyl)cyclobutanecarbonyl]amino}-5(S)-hydroxy-2(S)-isopropylhexyl)-2-(4-methoxybutoxy)benzamide hydrochloride, N-[4(S)-amino-5(S)-hydroxy-2(S)-isopropyl-6-(2-methyl-2-m-tolylpropionylamino)hexyl]-2-(4-methoxybutoxy)benzamide hydrochloride, N-[4(S)-amino-6-(2-cyclopentyl-2-methylpropionylamino)-S(S)-hydroxy-2(S)-isopropylhexyl]-2-(4-methoxybutoxy)benzamide hydrochloride, N-[4(S)-amino-5(S)-hydroxy-2(S)-isopropyl-6-(2-methyl-2-morpholin-4-ylpropionyl-amino)hexyl]-2-(4-methoxybutoxy)benzamide dihydrochloride, N-{4(S)-amino-6-[2-(3-fluorophenyl)-2-methylpropionylamino]-5(S)-hydroxy-2(S)-isopropylhexyl}-2-(4-methoxybutoxy)benzamide hydrochloride, N-{4(S)-amino-6-[(1-cyclohexylcyclobutanecarbonyl)amino]-5(S)-hydroxy-2(S)-isopropylhexyl}-2-(4-methoxybutoxy)benzamide hydrochloride, N-[4(S)-amino-5(S)-hydroxy-2(S)-isopropyl-6-(2-methyl-2-pyridin-3-ylpropionylamino)hexyl]-2-(4-methoxybutoxy)benzamide dihydrochloride, N-[4(S)-amino-6-(3-chloro-2,2-dimethylpropionylamino)-5(S)-hydroxy-2(S)-isopropylhexyl]-2-(4-methoxybutoxy)benzamide hydrochloride, N-[6-(2-acetylamino-2-methylpropionylamino)-4(S)-amino-5(S)-hydroxy-2(S)-isopropylhexyl]-2-(4-methoxybutoxy)benzamide hydrochloride, N-{4(S)-amino-5(S)-hydroxy-2(S)-isopropyl-6-[(1-trifluoromethylcyclobutanecarbonyl)-amino]hexyl}-2-(4-methoxybutoxy)benzamide hydrochloride, N-[4(S)-amino-6-(2-cyclohexyloxy-2-methylpropionylamino)-5(S)-hydroxy-2(S)-isopropylhexyl]-2-(4-methoxybutoxy)benzamide hydrochloride, N-[4(S)-amino-5(S)hydroxy-2(S)-isopropyl-6-(2-methoxy-2-methylpropionylamino)hexyl]-2-(4-methoxybutoxy)benzamide hydrochloride, N-[4(S)-amino-5(S)-hydroxy-2(S)-isopropyl-6-(2-methyl-2-piperidin-1-ylpropionyl-amino)hexyl]-2-(4-methoxybutoxy)benzamide dihydrochloride,
N-{4-amino-5-hydroxy-2-isopropyl-6-[(1-methylcyclohexanecarbonyl)amino]hexyl}-2-(4-methoxybutoxy)benzamide hydrochloride,
N-{4(S)-amino-5(S)-hydroxy-6-[2-(1H-indol-3-yl)-2-methylpropionylamino]-2(S)-isopropylhexyl}-2-(4-methoxybutoxy)benzamide hydrochloride,
N-[4(S)amino-5(S)-hydroxy-2(S)-isopropyl-6-(2-methoxypropionylamino)hexyl]-2-(4-methoxybutoxy)benzamide hydrochloride,
N-(3(S)-amino-2(S)-hydroxy-5(S)-{[2-(4-methoxybutoxy)benzoylamino]methyl}-6-methylheptyl)adamantane-1-carboxamide hydrochloride,
N-{4(S)-amino-6-[(2,2-dimethylpropionyl)hydroxyamino]-5(S)-hydroxy-2(S)-isopropylhexyl}-2-(4-methoxybutoxy)benzamide hydrochloride,
N-[4(S)-amino-6-(3,3-dimethylureido)-5(S)-hydroxy-2(S)-isopropylhexyl]-2-(4-methoxybutoxy)benzamide hydrochloride,
N-(4(S)-amino-6-benzoylamino-5(S)-hydroxy-2(S)-isopropylhexyl)-2-(4-methoxy-butoxy)benzamide hydrochloride,
N-[4(S)-amino-6-(formylisopropylamino)-5(S)-hydroxy-2(S)-isopropylhexyl]-2-(4-methoxybutoxy)benzamide hydrochloride,
N-[6-(acetylmethylamino)-4(S)-amino-5(S)-hydroxy-2(S)-isopropylhexyl]-2-(4-methoxy-butoxy)benzamide hydrochloride,
N-[4(S)-amino-5(S)-hydroxy-2(S)-isopropyl-6-(2-methyl-2-pyridin-2-ylpropionylamino)hexyl]-2-(4-methoxybutoxy)benzamide dihydrochloride,
N-[4(S)-amino-5(S)-hydroxy-2(S)-isopropyl-6-(2-methyl-2-piperidin-4-ylpropionyl-amino)hexyl]-2-(4-methoxybutoxy)benzamide dihydrochloride,
N-[4(S)-amino-5(S)-hydroxy-2(S)-isopropyl-6-(3,3,3-trifluoro-2(R)-methoxy-2-phenyl-propionylamino)hexyl]-2-(4-methoxybutoxy)benzamide hydrochloride,
N-[6-(N-acetylhydrazino)-4(S)-amino-5(S)-hydroxy-2(S)-isopropylhexyl]-2-(4-methoxy-butoxy)benzamide dihydrochloride,
N-[4(S)-amino-5(S)-hydroxy-2(S)-isopropyl-6-(2(R)-methoxy-3-phenylpropionylamino)hexyl]-2-(4-methoxybutoxy)benzamide hydrochloride,
N-[4(S)-amino-6-(3-cyclohexyl-2(R)-methoxypropionylamino)-5(S)-hydroxy-2(S)-isopropylhexyl]-2-(4-methoxybutoxy)benzamide hydrochloride,
N-[4(S)-amino-5(S)-hydroxy-2(S)-isopropyl-6-(2-methyl-2-piperidin-3(R)-ylpropionyl-amino)hexyl]-2-(4-methoxybutoxy)benzamide dihydrochloride,
N-[4(S)-amino-5(S)-hydroxy-2(S)-isopropyl-6-(2-methyl-2-piperidin-3(S)-ylpropionyl-amino)hexyl]-2-(4-methoxybutoxy)benzamide dihydrochloride,
N-{4(S)-amino-5(S)-hydroxy-6-[2-(1H-imidazol-4-yl)-2-methylpropionylamino]-2(S)-isopropylhexyl}-2-(4-methoxybutoxy)benzamide hydrochloride,
N-[4(S)-amino-6-(2,2-dimethyl-4-methylaminobutyrylamino)-5(S)-hydroxy-2(S)-isopropylhexyl]-2-(4-methoxybutoxy)benzamide dihydrochloride,
N-{4(S)-amino-5(S)-hydroxy-6-[(2(S)-hydroxy-(S)-cyclopentanecarbonyl)amino]-2(S)-isopropylhexyl}-2-(4-methoxybutoxy)benzamide hydrochloride,
N-[4(S)-amino-5(S)-hydroxy-2(S)-isopropyl-6-(2-methyl-2-piperidin-2(S)-ylpropionyl-amino)hexyl]-2-(4-methoxybutoxy)benzamide dihydrochloride,
N-[4(S)-amino-5(S)-hydroxy-2(S)-isopropyl-6-(2-methyl-2-piperidin-2(R)-ylpropionyl-amino)hexyl]-2-(4-methoxybutoxy)benzamide dihydrochloride,
N-[4(S)-amino-5(S)-hydroxy-2(S)-isopropyl-6-(2-methyl-2-(1,2-dihydrospiro[3H-indole-3,4'-piperidin]-1'-yl)propionylamino)hexyl]-2-(4-methoxybutoxy)benzamide dihydrochloride

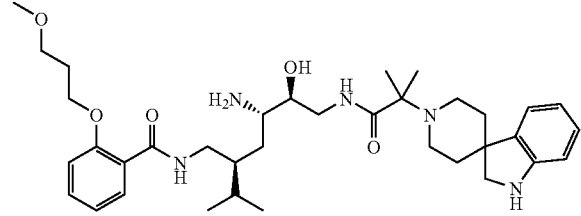

N-{4(S)-amino-5(S)-hydroxy-6-[2-(cis-4-hydroxycyclohex-1-yl)-2-methylpropionylamino]-2(S)-isopropylhexyl}-2-(4-methoxybutoxy)benzamide hydrochloride,
N-{4(S)-amino-5(S)-hydroxy-6-[2-(trans-4-hydroxycyclohex-1-yl)-2-methylpropionylamino]-2(S)-isopropylhexyl}-2-(4-methoxybutoxy)benzamide hydrochloride,
N-{4(S)-amino-5(S)-hydroxy-2(S)-isopropyl-6-[2-(cis-4-methoxycyclohex-1-yl)-2-methylpropionylamino]hexyl}-2-(4-methoxybutoxy)benzamide hydrochloride,
N-{4(S)-amino-5(S)-hydroxy-2(S)-isopropyl-6-[2-(trans-4-methoxycyclohex-1-yl)-2-methylpropionylamino]hexyl}-2-(4-methoxybutoxy)benzamide hydrochloride,
N-[4(S)-amino-6-(2-cyclohexyl-2(R)-methoxyacetylamino)-5(S)-hydroxy-2(S)-isopropylhexyl]-2-(4-methoxybutoxy)benzamide hydrochloride,
N-[4(S)-amino-5(S)-hydroxy-2(S)-isopropyl-6-(2(R)-methoxy-2-phenylacetylamino)hexyl]-2-(4-methoxybutoxy)benzamide hydrochloride,
N-[4(S)-amino-5(S)-hydroxy-2(S)-isopropyl-6-(2(R)-methoxy-3,3-dimethylbutyryl-amino)hexyl]-2-(4-methoxybutoxy)benzamide hydrochloride,
N-[4(S)-amino-5(S)-hydroxy-2(S)-isopropyl-6-(3,3,3-trifluoro-2-methoxy-2-trifluoromethylpropionylamino)hexyl]-2-(4-methoxybutoxy)benzamide hydrochloride,
N-[4(S)-amino-5(S)-hydroxy-2(S)-isopropyl-6-(3,3,3-trifluoro-2(R)-methoxy-2-methyl-propionylamino)hexyl]-2-(4-methoxybutoxy)benzamide hydrochloride,
N-[4(S)-amino-5(S)-hydroxy-2(S)-isopropyl-6-(3,3,3-trifluoro-2(S)-methoxy-2-methyl-propionylamino)hexyl]-2-(4-methoxybutoxy)benzamide hydrochloride,
N-[4(S)-amino-6-(2-cyclohexyl-3,3,3-trifluoro-2(R)-methoxypropionylamino)-5(S)-hydroxy-2(S)-isopropylhexyl]-2-(4-methoxybutoxy)benzamide hydrochloride,
N-[4(S)-amino-5(S)-hydroxy-2(S)-isopropyl-6-(2(R)-methoxy-2-phenylpropionylamino)hexyl]-2-(4-methoxybutoxy)benzamide hydrochloride,
N-[4(S)-amino-6-(2-cyclohexyl-2(R)-methoxypropionylamino)-5(S)-hydroxy-2(S)-isopropylhexyl]-2-(4-methoxybutoxy)benzamide hydrochloride,
N-{4(S)-amino-5(S)-hydroxy-2(S)-isopropyl-6-[(1-methoxycyclopentanecarbonyl)-amino]hexyl}-2-(4-methoxybutoxy)benzamide hydrochloride,
N-{4(S)-amino-5(S)-hydroxy-2(S)-isopropyl-6-[(1-methoxycyclohexanecarbonyl)amino]hexyl}-2-(4-methoxybutoxy)benzamide hydrochloride, N-[4(S)-Amino-5(S)-hydroxy-2(S)-isopropyl-6-(2-methyl-2-piperidin-3(R,S)-yl-N-{4(S)-Amino-5(S)-hydroxy-2(S)-isopropyl-6-[2-methyl-2-(1-methyl-piperidin-3(R,S)-yl)-propionylamino]-hexyl}-2-(4-methoxy-butoxy)-benzamide dihydrochloride, N-[4(S)-Amino-5(S)-hydroxy-2(S)-isopropyl-6-(2-methyl-2-piperidin-2(R,S)-yl-propionylamino)-hexyl]-2-(4-methoxy-butoxy)-benzamide dihydrochloride, N-{4(S)-Amino-5(S)-hydroxy-2(S)-isopropyl-6-[2-methyl-2-(1-methyl-piperidin-2(R,S)-yl)-propionylamino]-hexyl}-2-(4-methoxy-butoxy)-benzamide dihydrochloride, N-{4(S)-Amino-5(S)-hydroxy-6-[2(R,S)-(trans-2-hydroxy-cyclohexyl)-2-methyl-propionylamino]-2(S)-isopropyl-hexyl}-2-(4-methoxy-butoxy)-benzamide hydrochloride, N-{4(S)-Amino-5(S)-hydroxy-6-[2-(3(S)-hydroxy-cyclohex-1(R)-yl)-2-methyl-propionylamino]-2(S)-isopropyl-hexyl}-2-(4-methoxy-butoxy)-benzamide hydrochloride, N-[4(S)-Amino-5(S)-hydroxy-6-(2-imidazol-1-yl-2-methyl-propionylamino)-2(S)-isopropyl-hexyl]-2-(4-methoxy-butoxy)-benzamide dihydrochloride, N-[4(S)-Amino-6-(2-cyano-2,2-dimethyl-acetylamino)-5(S)-hydroxy-2(S)-isopropyl-hexyl]-2-(4-methoxy-butoxy)-benzamide hydrochloride, N-{6-[trans-2-(4-Acetylamino-cyclohexyl)-2-methyl-propionylamino]-4(S)-amino-5(S)-hydroxy-2(S)-isopropyl-hexyl}-2-(4-methoxy-butoxy)-benzamide hydrochloride, N-{6-[2-(3(S)-Acetylamino-cyclohex-1(R)-yl)-2-methyl-propionylamino]-4(S)-amino-5(S)-hydroxy-2(S)-isopropyl-hexyl}-2-(4-methoxy-butoxy)-benzamide hydrochloride, N-[4(S)-Amino-6-(2,2-difluoro-2-phenyl-acetylamino)-5(S)-hydroxy-2(S)-isopropyl-hexyl]-2-(4-methoxy-butoxy)-benzamide hydrochloride, N-[4(S)-Amino-6-(2-cyclohexyl-2,2-difluoro-acetylamino)-5(S)-hydroxy-2(S)-isopropyl-hexyl]-2-(4-methoxy-butoxy)-benzamide hydrochloride, N-{4(S)-Amino-6-[2,2-difluoro-2-(tetrahydro-pyran-4-yl)-acetylamino]-5(S)-hydroxy-2(S)-isopropyl-hexyl}2-(4-methoxy-butoxy)-benzamide hydrochloride, N-[4(S)-Amino-5(S)-hydroxy-2(S)-isopropyl-6-(2-oxopiperidin-1-yl)hexyl]-2-(3-methoxy-propoxy)benzamide hydrochloride

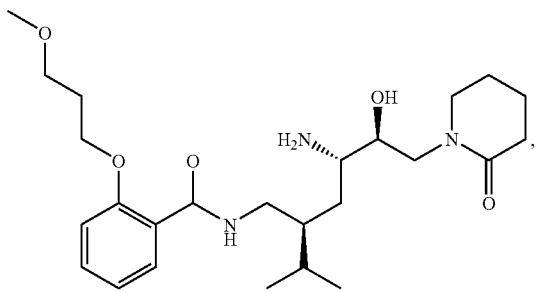

N-[4(S)-amino-5(S)-hydroxy-2(S)-isopropyl-6-(2-oxopiperidin-1-yl)hexyl]-2-(4-methoxy-butoxy)benzamide hydrochloride, N-[4(S)-amino-6-(3,3-dimethyl-2-oxopyrrolidin-1-yl)-5(S)-hydroxy-2(S)-isopropylhexyl]-2-(4-methoxybutoxy)benzamide hydrochloride, N-[4(S)-amino-5(S)-hydroxy-2(S)-isopropyl-6-(2-oxoazepan-1-yl)hexyl]-2-(4-methoxy-butoxy)benzamide hydrochloride, N-[4(S)-amino-6-(3,3-dimethyl-2-oxoazepan-1-yl)-5(S)-hydroxy-2(S)-isopropylhexyl]-2-(4-methoxybutoxy)benzamide hydrochloride, N-[4(S)-amino-5(S)-hydroxy-6-(4-hydroxy-2-oxopyrrolidin-1-yl)-2(S)-isopropylhexyl]-2-(4-methoxybutoxy)benzamide hydrochloride, N-[4(S)-amino-5(S)-hydroxy-2(S)-isopropyl-6-(2-oxotetrahydropyrimidin-1-yl)hexyl]-2-(4-methoxybutoxy)benzamide hydrochloride, N-[4(S)-Amino-5(S)-hydroxy-2(S)-isopropyl-6-(propane-2-sulphonylamino)hexyl]-2-(3-methoxypropoxy)benzamide hydrochloride

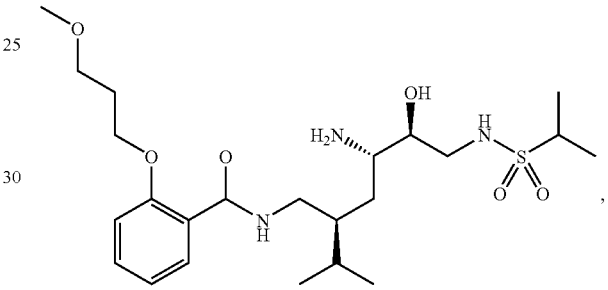

N-[4(S)-amino-5(S)-hydroxy-2(S)-isopropyl-6-(propane-2-sulphonylamino)hexyl]-2-(4-methoxybutoxy)benzamide hydrochloride, N-(4(S)-amino-6-cyclopropanesulphonylamino-5(S)-hydroxy-2(S)-isopropylhexyl)-2-(4-methoxybutoxy)benzamide hydrochloride, N-(4(S)-amino-5(S)-hydroxy-2(S)-isopropyl-6-phenylmethanesulphonylaminohexyl)-2-(4-methoxybutoxy)benzamide hydrochloride, N-[4(S)-amino-5(S)-hydroxy-2(S)-isopropyl-6-(thiophene-2-sulphonylamino)hexyl]-2-(4-methoxybutoxy)benzamide hydrochloride, N-(4(S)-amino-6-benzenesulphonylamino-5(S)-hydroxy-2(S)-isopropylhexyl)-2-(4-methoxybutoxy)benzamide hydrochloride, N-[4(S)-Amino-5(S)-hydroxy-2(S)-isopropyl-6-(2-methyl-propane-2-sulfonylamino)-hexyl]-2-(4-methoxy-butoxy)-benzamide hydrochloride and N-[4(S)-Amino-6-(2-cyclohexyl-propane-2-sulfonylamino)-5(S)-hydroxy-2(S)-isopropyl-hexyl]-2-(4-methoxy-butoxy)-benzamide hydrochloride.

2. A pharmaceutical composition comprising, as an active pharmaceutical ingredient, a compound according to claim 1 in free form or as a pharmaceutically usable salt, and a pharmaceutically inert, inorganic or organic excipient.

* * * * *